United States Patent
Ben-Haim

(10) Patent No.: US 10,493,294 B2
(45) Date of Patent: Dec. 3, 2019

(54) DETECTION OF REDUCED-CONTROL CARDIAC ZONES

(71) Applicant: Tylerton International Inc., Road Town, Tortola (VG)

(72) Inventor: Shlomo Ben-Haim, Marlow (GB)

(73) Assignee: Tylerton International Inc., Road Town (VG)

( * ) Notice: Subject to any disclaimer, the term of this patent is extended or adjusted under 35 U.S.C. 154(b) by 0 days.

(21) Appl. No.: 16/000,962

(22) Filed: Jun. 6, 2018

(65) Prior Publication Data
US 2018/0280713 A1 Oct. 4, 2018

Related U.S. Application Data

(63) Continuation of application No. 14/917,285, filed as application No. PCT/IB2014/064316 on Sep. 8, 2014, now Pat. No. 10,052,495, which is a continuation-in-part of application No. PCT/IL2014/050086, filed on Jan. 24, 2014, and a
(Continued)

(51) Int. Cl.
| | |
|---|---|
| *A61B 6/00* | (2006.01) |
| *G06T 7/00* | (2017.01) |
| *A61N 2/00* | (2006.01) |
| *A61B 6/03* | (2006.01) |
| *A61N 2/02* | (2006.01) |

(Continued)

(52) U.S. Cl.
CPC ............. *A61N 2/006* (2013.01); *A61B 6/037* (2013.01); *A61B 6/506* (2013.01); *A61N 2/02* (2013.01); *G06T 7/0012* (2013.01); *G06T 7/0014* (2013.01); *A61B 34/10* (2016.02);

*A61B 2018/00577* (2013.01); *G06T 2207/10072* (2013.01); *G06T 2207/10076* (2013.01); *G06T 2207/30016* (2013.01); *G06T 2207/30048* (2013.01); *G06T 2207/30092* (2013.01)

(58) Field of Classification Search
CPC .................................. A61B 6/00; G06T 7/00
USPC .......................... 382/128–134; 600/300, 547
See application file for complete search history.

(56) References Cited

U.S. PATENT DOCUMENTS

| | | |
|---|---|---|
| 5,077,035 A | 12/1991 | Wieland et al. |
| 5,789,420 A | 8/1998 | Efange et al. |

(Continued)

FOREIGN PATENT DOCUMENTS

| | | |
|---|---|---|
| CN | 1981710 | 6/2007 |
| CN | 101005874 | 7/2007 |

(Continued)

OTHER PUBLICATIONS

Communication Pursuant to Article 94(3) EPC dated Mar. 13, 2018 From the European Patent Office Re. Application No. 14841866.8. (13 Pages).

(Continued)

*Primary Examiner* — Abolfazl Tabatabai

(57) ABSTRACT

A method of treating cardiac arrhythmia in a heart, including (i) determining that cardiac tissue is viable but with reduced innervation; and (ii) ablating the tissue to reduce a prevalence of arrhythmia in said heart. Optionally, the determining comprises detecting portions of heart wall which lack electrical activity. Optionally, at least some tissue which is viable but lacks nervous control is ablated, for example, to reduce or avoid arrhythmia.

18 Claims, 20 Drawing Sheets

Related U.S. Application Data continuation-in-part of application No. PCT/IL2014/050088, filed on Jan. 24, 2014, and a continuation-in-part of application No. PCT/IL2014/050089, filed on Jan. 24, 2014, and a continuation-in-part of application No. PCT/IL2014/050090, filed on Jan. 24, 2014, and a continuation-in-part of application No. PCT/IL2014/050246, filed on Mar. 11, 2014.

(60) Provisional application No. 61/875,069, filed on Sep. 8, 2013, provisional application No. 61/875,070, filed on Sep. 8, 2013, provisional application No. 61/875,074, filed on Sep. 8, 2013, provisional application No. 61/925,670, filed on Jan. 10, 2014, provisional application No. 61/925,669, filed on Jan. 10, 2014, provisional application No. 62/003,108, filed on May 27, 2014, provisional application No. 62/030,740, filed on Jul. 30, 2014, provisional application No. 62/030,972, filed on Jul. 30, 2014, provisional application No. 62/030,917, filed on Jul. 30, 2014.

(51) Int. Cl.
*A61B 34/10* (2016.01)
*A61B 18/00* (2006.01)

(56) References Cited

U.S. PATENT DOCUMENTS

| | | | |
|---|---|---|---|
| 6,211,360 B1 | 4/2001 | Glick et al. | |
| 6,358,492 B1 | 3/2002 | Kuhar et al. | |
| 6,490,480 B1 * | 12/2002 | Lerner | |
| 6,511,500 B1 | 1/2003 | Rahme | |
| 6,845,267 B2 | 1/2005 | Harrison et al. | |
| 7,363,076 B2 | 4/2008 | Yun et al. | |
| 7,769,441 B2 * | 8/2010 | Foreman | A61N 1/36114 607/2 |
| 8,359,092 B2 | 1/2013 | Hayam et al. | |
| 8,364,285 B2 | 1/2013 | Rezai | |
| 8,440,168 B2 | 5/2013 | Yang et al. | |
| 9,566,447 B2 * | 2/2017 | Meyer | A61N 1/36114 |
| 2004/0138550 A1 | 7/2004 | Hartlep et al. | |
| 2005/0004465 A1 | 1/2005 | Abuhamad | |
| 2005/0008126 A1 | 1/2005 | Juh et al. | |
| 2005/0080327 A1 | 4/2005 | Jenkins et al. | |
| 2005/0215889 A1 | 9/2005 | Patterson, II | |
| 2005/0261672 A1 | 11/2005 | Deem et al. | |
| 2006/0085049 A1 | 4/2006 | Cory et al. | |
| 2006/0127309 A1 | 6/2006 | Raffel et al. | |
| 2006/0287648 A1 | 12/2006 | Schwartz | |
| 2007/0016028 A1 | 1/2007 | Donaldson et al. | |
| 2007/0049817 A1 | 3/2007 | Preiss et al. | |
| 2007/0106337 A1 | 5/2007 | Errico et al. | |
| 2007/0127793 A1 | 6/2007 | Beckett et al. | |
| 2008/0146914 A1 | 6/2008 | Polzin et al. | |
| 2008/0161803 A1 | 7/2008 | Oral et al. | |
| 2008/0279436 A1 | 11/2008 | Razifar et al. | |
| 2009/0192393 A1 | 7/2009 | Hayam et al. | |
| 2009/0192394 A1 | 7/2009 | Guttag et al. | |
| 2010/0193696 A1 | 8/2010 | Blevis et al. | |
| 2010/0221182 A1 | 9/2010 | Purohit et al. | |
| 2010/0268289 A1 | 10/2010 | Chen et al. | |
| 2010/0312128 A1 | 12/2010 | Karst et al. | |
| 2011/0087088 A1 | 4/2011 | Korn et al. | |
| 2011/0144723 A1 | 6/2011 | Streeter et al. | |
| 2011/0152974 A1 | 6/2011 | Rezai et al. | |
| 2011/0189096 A1 | 8/2011 | Watanabe et al. | |
| 2011/0218818 A1 | 9/2011 | Butson et al. | |
| 2011/0230775 A1 | 9/2011 | Barley et al. | |
| 2011/0238128 A1 | 9/2011 | Dobak, III | |
| 2011/0306846 A1 | 12/2011 | Osorio | |
| 2012/0065492 A1 | 3/2012 | Gertner et al. | |
| 2012/0155733 A1 | 6/2012 | Wagenknecht | |
| 2012/0271171 A1 | 10/2012 | Gertner | |
| 2013/0072790 A1 | 3/2013 | Ludwig et al. | |
| 2013/0116681 A1 | 5/2013 | Zhang | |
| 2013/0123773 A1 | 5/2013 | Schwartz | |
| 2013/0131746 A1 | 5/2013 | Simon et al. | |
| 2015/0327805 A1 | 11/2015 | Ben-Haim | |
| 2015/0351834 A1 | 12/2015 | Ben-Haim et al. | |
| 2015/0359430 A1 | 12/2015 | Ben-Haim | |
| 2015/0366523 A1 | 12/2015 | Ben-Haim | |
| 2016/0027342 A1 | 1/2016 | Ben Haim | |
| 2016/0217571 A1 | 7/2016 | Ben-Haim | |
| 2016/0220835 A1 | 8/2016 | Ben-Haim | |
| 2016/0331337 A1 | 11/2016 | Ben Haim | |

FOREIGN PATENT DOCUMENTS

| | | |
|---|---|---|
| CN | 101048194 | 10/2007 |
| CN | 101137326 | 3/2008 |
| CN | 101219058 | 7/2008 |
| CN | 101687780 | 3/2010 |
| CN | 101859641 | 10/2010 |
| CN | 102120039 | 7/2011 |
| CN | 102223838 | 10/2011 |
| CN | 102740769 | 10/2012 |
| EP | 1733692 | 12/2006 |
| EP | 2474526 | 7/2012 |
| EP | 2591722 | 5/2013 |
| JP | 2007-144175 | 6/2007 |
| JP | 2008-149147 | 7/2008 |
| JP | 2008-259696 | 10/2008 |
| JP | 2010-514786 | 5/2010 |
| JP | 2010-178949 | 8/2010 |
| JP | 2012-509701 | 4/2012 |
| JP | 2013-103134 | 5/2013 |
| KR | 20090074399 | 7/2009 |
| WO | WO 01/82978 | 11/2001 |
| WO | WO 02/102238 | 12/2002 |
| WO | WO 2005/053615 | 6/2005 |
| WO | WO 2007/002541 | 1/2007 |
| WO | WO 2008/009021 | 1/2008 |
| WO | WO 2008/083056 | 7/2008 |
| WO | WO 2008/121578 | 10/2008 |
| WO | WO 2009/022271 | 2/2009 |
| WO | WO 2010/058372 | 5/2010 |
| WO | WO 2011/046879 | 4/2011 |
| WO | WO 2011/091069 | 7/2011 |
| WO | WO 2011/110959 | 9/2011 |
| WO | WO 2012/011036 | 1/2012 |
| WO | WO 2012/061153 | 5/2012 |
| WO | WO 2013/036869 | 3/2013 |
| WO | WO 2014/115148 | 7/2014 |
| WO | WO 2014/115150 | 7/2014 |
| WO | WO 2014/115151 | 7/2014 |
| WO | WO 2014/115152 | 7/2014 |
| WO | WO 2014/141247 | 9/2014 |
| WO | WO 2015/033317 | 3/2015 |
| WO | WO 2015/033319 | 3/2015 |
| WO | WO 2015/104672 | 7/2015 |
| WO | WO 2015/181753 | 12/2015 |

OTHER PUBLICATIONS

Communication Relating to the Results of the Partial International Search dated Apr. 16, 2015 From the International Searching Authority Re. Application No. PCT/IB2015/050148.

International Preliminary Report on Patentability dated Aug. 6, 2015 From the International Bureau of WIPO Re. Application No. PCT/IL2014/050086.

International Preliminary Report on Patentability dated Aug. 6, 2015 From the International Bureau of WIPO Re. Application No. PCT/IL2014/050088.

International Preliminary Report on Patentability dated Aug. 6, 2015 From the International Bureau of WIPO Re. Application No. PCT/IL2014/050089.

International Preliminary Report on Patentability dated Aug. 6, 2015 From the International Bureau of WIPO Re. Application No. PCT/IL2014/050090.

(56) References Cited

OTHER PUBLICATIONS

International Preliminary Report on Patentability dated Dec. 8, 2016 From the International Bureau of WIPO Re. Application No. PCT/IB2015/053984. (11 Pages).
International Preliminary Report on Patentability dated Mar. 17, 2016 From the International Bureau of WIPO Re. Application No. PCT/IB2014/064316.
International Preliminary Report on Patentability dated Mar. 17, 2016 From the International Bureau of WIPO Re. Application No. PCT/IB2014/064319.
International Preliminary Report on Patentability dated Jul. 21, 2016 From the International Bureau of WIPO Re. Application No. PCT/IB2015/050148.
International Preliminary Report on Patentability dated Sep. 24, 2015 From the International Bureau of WIPO Re. Application No. PCT/IL2014/050246.
International Search Report and the Written Opinion dated Oct. 1, 2015 From the International Searching Authority Re. Application No. PCT/IB2015/053984.
International Search Report and the Written Opinion dated Jun. 5, 2014 From the International Searching Authority Re. Application No. PCT/IL2014/050086.
International Search Report and the Written Opinion dated Jun. 9, 2014 From the International Searching Authority Re. Application No. PCT/IL2014/050088.
International Search Report and the Written Opinion dated Jun. 10, 2014 From the International Searching Authority Re. Application No. PCT/IL2014/050089.
International Search Report and the Written Opinion dated May 15, 2014 From the International Searching Authority Re. Application No. PCT/IL2014/050090.
International Search Report and the Written Opinion dated Feb. 20, 2015 From the International Searching Authority Re. Application No. PCT/IB2014/064316.
International Search Report and the Written Opinion dated Feb. 25, 2015 From the International Searching Authority Re. Application No. PCT/IB2014/064319.
International Search Report and the Written Opinion dated Jul. 27, 2015 From the International Searching Authority Re. Application No. PCT/IB2015/050148.
International Search Report and the Written Opinion dated Jul. 28, 2014 From the International Searching Authority Re. Application No. PCT/IL2014/050246.
Invitation to Pay Additional Fees Dated Apr. 10, 2014 From the International Searching Authority Re. Application No. PCT/IL2014/050090.
Invitation to Pay Additional Fees Dated Dec. 16, 2014 From the International Searching Authority Re. Application No. PCT/IB2014/064319.
Invitation to Pay Additional Fees Dated Dec. 23, 2014 From the International Searching Authority Re. Application No. PCT/IB2014/064316.
Notice of Allowance dated Feb. 21, 2018 From the U.S. Appl. No. 14/917,285. (8 pages).
Notice of Reason for Rejection dated May 9, 2017 From the Japan Patent Office Re. Application No. 2015-554307 and Its Translation Into English. (16 Pages).
Notification of Office Action and Search Report dated Dec. 2, 2016 From the State Intellectual Property Office of the People's Republic of China Re. Application No. 201480005617.0 and Its Summary in English.
Notification of Office Action and Search Report dated Jul. 14, 2017 From the State Intellectual Property Office of the People's Republic of China Re. Application No. 201480058535.2. (8 Pages).
Official Action dated Jan. 6, 2017 From the U.S. Appl. No. 14/762,933. (55 pages).
Official Action dated Aug. 10, 2017 From the U.S. Appl. No. 14/762,933. (47 pages).
Official Action dated Jun. 26, 2017 From the U.S. Appl. No. 14/917,285. (35 pages).

Supplementary European Search Report and the European Search Opinion dated Jan. 4, 2016 From the European Patent Office Re. Application No. 14743474.0.
Supplementary European Search Report and the European Search Opinion dated Feb. 9, 2016 From the European Patent Office Re. Application No. 14743909.5. (9 Pages).
Supplementary European Search Report and the European Search Opinion dated Jun. 19, 2017 From the European Patent Office Re. Application No. 14841866.8. (11 Pages).
Abi-Jaoudeh et al. "Multimocality Image Fusion-Guided Procedures: Technique, Accuracy, and Applications", Cardiovascular and Interventional Radiology, 35(5): 986-998, Published Online Aug. 1, 2012.
Arora "Recent Insights Into the Role of the Autonomic Nervous System in the Creation of Substrate for Atrial Fibrillation—Implications for Therapies Targeting the Atrial Autonomic Nervous System", Circulation: Arrhythmia and Electrophysiology, XP055236980, 5(4): 850-859, Aug. 1, 2012. p. 6, 7, Chapter 'Recent Developments in Imaging of the Autonomic Innervation of the Atria—Implications for AF Ablation'.
Arora et al. "Porcine Intrinsic Cardiac Ganglia", The Anatomical Record Part A, 271A: 249-258, 2003.
Bercier et al. "Multimodality Image Fusion for Radiosurgery Localisation of Large AVMs", Proceedings of the 22nd Annual International Conference of the IEEE Engineering in Medicine and Biology Society, EMBS, Chicago, IL, USA, Jul. 23-29, 2000, XP002422677, 4: 2689-2692, Jul. 23, 2000.
Biosensors International Group "D-SPECT™ Cardiac Imaging System", Biosensors International Group, Ltd., Product Description, 2 P., 2013.
Burnstock "Autonomic Neurotransmission: 60 Years Since Sir Henry Dale", The Annual Review of Pharmacology and Toxicology, 49: 1-30, 2009.
Dilsizian et al. "Current Diagnostic Techniques of Assessing Myocardial Viability in Patients With Hibernating and Stunned Myocardium", Circulation, XP055375410, 87(1): 1-20, Jan. 1993.
Ernst et al. "Image Guided Ablation of Ganglionated Plexi as an Additional to PV Isolation—Follow-Up Results of the Initial Case Series", Heart Rhythm, XP029240122, 12(5/Suppl.): S434-S435, Poster Session V, # P005-83, May 2015.
Esler et al. "Sympathetic Nerve Activity and Neurotransmitter Release in Humans: Translation From Pathophysiology Into Clinical Practice", Acta Physiologica Scandinavica, 177: 275-284, 2003.
Flotats et al. "Proposal for Standardization of 123I-Metaiodobenzylguanidine (MIBG) Cardiac Sympathetic Imaging by the EANM Cardiovascular Committee and the European Council of Cardiology", European Journal of Nuclear Medicine and Molecular Imaging, 37(9): 1802-1812, Aug. 2010.
Gering et al. "An Integrated Visualization System for Surgical Planning and Guidance Using Image Fusion and an Open MR", Journal of Magnetic Resonance Imaging, XP002239881, 13(6): 967-975, Jun. 2001.
Ghosh et al. "Assessment of Myocardial Ischaemia and Viability: Role of Positron Emission Tomography", European Heart Journal, XP055181382, 31(24): 2984-2995, Online Publish-Ahead-of Print Oct. 21, 2010. p. 2986, col. 1, p. 2990-2993, col. 2.
Hirsch et al. "Measuring Activity of the Autonomic Nervous System in Humans", Obesity Research, 11(1): 2-4, Jan. 2003.
Hu et al. "Dynamic Molecular Imaging of Cardiac Innervation Using a Dual Head Pinhole SPECT System", Lawrence Berkely National Laboratory, University of California, eScholarship, XP055214624, LBNL Report No. LBNL-60008, p. 1-54, May 23, 2008. Abstract, p. 16, Para 3-p. 20, Para 2, Figs.9, 10, Table 2.
Iaea "Technetium-99m Radiopharmaceuticals: Status and Trends", IAEA, International Atomic Energy Agency Radioisotopes and Radiopharmaceuticals Series, 1: 1-378, 2009.
Katafuchi "Cardiac Radionuclide Imaging", Japanese Journal of Radiological Technology, 64(5): 626-637, 2008. & English Abstract.
Klein et al. "Abstract 17871: Assessment of Global Cardiac Innervation Using 1123-Meta-Iodobenzylguanidine Before and After Ventricular Tachycardia Ablation", Circulation, 126(Suppl.21): # 17871, Nov. 20, 2012.

(56) References Cited

OTHER PUBLICATIONS

Klein et al. "Assessment of Myocardial Viability With Contrast-Enhanced Magnetic Resonance Imaging: Comparison With Positron Emission Tomography", Circulation, XP055375416, 105(2): 162-167, Jan. 15, 2002.
Knuepfer et al. "Direct Assessment of Organ Specific Sympathetic Nervous System Activity in Normal and Cardiovascular Disease States", Experimental Physiology, 95(1): 32-33, 2010.
Knuuti et al. "Myocardial Viability: Fluorine-10-Deoxyglucose Positron Emission Tomography in Prediction of Wall Motion Recovery After Revascularization", American Heart Journal, XP023288264, 127(4): 785-796, Apr. 1994.
Kosa et al. "Principles and Methods of Myocardial Perfusion Imaging", Chap.2: 33-57.
Langer et al. "PET and SPET Tracers for Mapping the Cardiac Nervous System", European Journal of Nuclear Medicine and Molecular Imaging, 29(3): 416-434, Mar. 2002.
Lemery et al. "Feasibility Study of Endocardial Mapping of Ganglionated Plexuses During Catheter Ablation of Atrial Fibrillation", Heart Rhythm, X024972538, 3(4): 387-396, Apr. 2006. p. 395, Left Col., Lines 3-30, Fig.2, p. 388, col. 1, Line 11—p. 389, col. 1, Line 3.
Levin et al. "Techniques for Efficient, Real-Time, 3D Visualization of Multi-Modality Cardiac Data Using Consumer Graphics Hardware", Computerized Medical Imaging and Graphics, 29(6): 463-475, Sep. 30, 2005.
Linz et al. "Atrial Autonomic Innervation: A Target for Interventional Antiarrhythmic Therapy?", Journal of the American College of Cardiology, JACC, p. 1-33, 2013.
Malliani et al. "Emerging Excitatory Role of Cardiovascular Sympathetic Afferents in Pathophysiological Conditions", Hypertension, 39: 63-68, Jan. 2002.
Mallouhi et al. "3 T MR Tomography of the Brachial Plexus: Structural and Microstructural Evaluation", European Journal of Radiology, 81(9): 2231-2245, Sep. 30, 2012.
Malpas "Sympathetic Nervous System Overactivity and Its Role in the Development of Cardiovascular Disease", Physiology Review, 90: 513-557, 2010.
Manssour et al. "Visualizing Inner Structures in Multimodel Volume Data", Proceedings of the 15th Brazilian Symposium on Computer Graphics and Image Processing (SIBGRAPI'02), Oct. 7-10, 2002, p. 51-58, Oct. 7, 2002.
Matsunari et al. "Iodine-123 Metaiodobenzylguanidinen Imaging and Carbon-11 Hydroxyephedrine Positron Emission Tomography Compared in Patients With Left Ventricular Dysfunction", Circulation Cardiovascular Imaging, 3: 595-603, Sep. 2010.
Mourot et al. "Effects of the Cold Pressor Test on Cardiac Autonomic Control in Normal Subjects", Physiology Research, 58: 83-91, 2009.
Rabinovitch et al. "A Method of Dynamic Analysis of Iodine-123-Metaiodobenzylguanidine Scintigrams in Cardiac Mechanical Overload Hypertrophy and Failure", Journal of Nuclear Medicine, XP055214626, 34(4): 589-600, Apr. 1993. p. 589, col. 1-p. 593, col. 2, p. 598, col. 2-p. 599, col. 1.
Raffel et al. "Quantification of Cardiac Sympathetic Nerve Density With N-11C-Guanyl-Meta-Octopamine and Tracer Kinetic Analysis", The Journal of Nuclear Medicine, XP055214628, 54(9): 1645-1652, Published Online Jul. 25, 2013. p. 1645, col. 1-p. 1647, col. 1, Figs.1, 2.
Rispler et al. "Quantitative 123I-MIBG SPECT/CT Assessment of Cardiac Sympathetic Innervation—A New Diagnostic Tool for Heart Failure", International Journal of Cardiology, XP028740607, 168(2): 1556-1558, Jan. 17, 2013. p. 1556, col. 1-p. 1558, col. 1.
Ross et al. "Research Applications of Selected [123]I-Labeled Neuroreceptor SPECT Imaging Ligands", Journal of Nucelar Medicine and Technology, 32(4): 209-214, Dec. 2004.
San Mauro et al. "Nerves of the Heart: A Comprehensive Review With a Clinical Point of View", Neuroanatomy, 8: 28-31, 2009.
Sasano et al. "Abnormal Sympathetic Innervation of Viable Myocardium and the Substrate of Ventricular Tachycardia After Myocardial Infarction", Journal of the American College of Cardiology, 51(23): 2266-2275, Jun. 10, 2008.
Sciagra et al. "Rest-Redistribution Thallium-201 SPECT to Detect Myocardial Viability", The Journal of Nuclear Medicine, XP055181381, 39(3): 384-390, Mar. 1998. p. 384-389, Abstract/39/3/384, p. 384-389.
Sen "Some Observations of Decapsulation and Denervation of the Kidney", The British Journal of Urology, 8(4): 319-328, 1936.
Shabana et al. "Myocardial Viability: What We Know and What Is New", Cardiology Research and Practice, XP055375407, 2012(Art. ID 607486): Jan. 1-13, 2012. p. 3, r-h Col., Last Para.
Shoda "Catheter Ablation for Atrial Fibrillation in Patients With Heart Failure", Japanese Journal of Electrocardiology, 31(2): 205-207, 2011.
Singh "Chemistry, Design, and Structure-Activity Relationship of Cocaine Antagonists", Chemical Reviews, 100: 925-1024, 2000.
Sisson et al. "Metaiodobenzylguanidine to Map Scintigraphically the Adrenergic Nervous System in Man", The Journal of Nuclear Medicine, 28(10): 1625-1636, Oct. 1987.
Smith "Extrinsic Inputs to Intrinsic Neurons in the Porcine Heart In Vitro", The American Journal of Physiology, 276(2/Pt.2): R455-R467, Feb. 1999.
Smith et al. "Simulation of Cardiovascular System Diseases by Including the Autonomic Nervous System Into a Minimal Model", Computer Methods and Programs in Biomedicine, 86(2): 153-160, May 2007.
Stefanelli et al. "[123]I-MIBG Scintigraphy as a Powerful Tool to Plan an Implantable Cardioverter Defibrillator and to Assess Cardiac Resynchronization Therapy in Heart Failure Patients", International Journal of Molecular Imaging, XP055214933, 2012(Art. 690468): 1-6, Published Online Sep. 26, 2012. Abstract, p. 1, col. 1-p. 2, col. 1.
Sumiyoshi "New Diagnostic Methods and Non Pharmacological Therapies in Cardiac Arrhythmias", Juntendo Medical Journal, 42(4): 450-458, 1997.
Tan et al. "Autonomic Nerves in Pulmonary Veins", Heart Rythm, 4(3 Suppl.): S57-S60, Mar. 2007.
Travin "Cardiac Autonomic Imaging With SPECT Tracers", Journal of Nuclear Cardiology, 20(1): 128-143, Feb. 2013.
Troisi et al. "Relation of Obesity and Diet Sympathetic Nervous System Activity", Hypertension, 17(5): 669-677, May 1991.
Underwood et al. "Imaging Techniques for the Assessment of Myocardial Hibernation. Report of a Study Group of European Society of Cardiology", ACC Current Journal Review, XP004655395, 13(9): 23, Sep. 2004.
University of Ottawa View of NCT02071680 on Feb. 25, 2014: Nuclear Imaging Using 123I-mIBG (Adreview™ GE Healthcare) to Visually Identify Atrial Cardiac Innervation, ClinicalTrials.gov Archive, University of Ottawa Heart Insitute, XP0055214861, 4 P., Feb. 25, 2014. p. 1-3.
Unknown "SPECT CT Fusion Image", Imaging Diagnosis in Nuclear Medicine, 24(1): 52-59, 2009. Partial English Translation.
Vallabhajosula et al. "Radioiodinated Metaiodobenzylguanidine (MIBG): Radiochemistry, Biology, and Pharmacology", Seminars in Nuclear Medicine, 41: 324-333, 2011.
Vissing et al. "Stimulation of Skin Sympathetic Nerve Discharge by Central Command", Circulation Research, 69(1): 228-238, Jul. 1991.
Wang et al. "Metaiodobenzylguanidine Myocardial Imaging and the Application Thereof", Foreign Medical Sciences, Section of Internal Medicine, 28(5): 081511165-E-1-081511165-E-8, May 2001. & English Translation.
Wong et al. "Pericardial Fat is Associated With Atrial Fibrillation Severity and Ablation Outcome", Journal of the American College of Cardiology, JACC, 57(17): 1745-1751, 2011.
Zhang et al. "The Celiac Ganglia: Anatomic Study Using MRI in Cadavers", American Journal of Roentgenology, AJR, 186(6): 1520-1523, Jun. 2006.
Miranda et al. "Sustained Ventricular Tachycardia is Associated With Regional Myocardial Sympathetic Denervation Assessed With

(56) References Cited

OTHER PUBLICATIONS

[123]I-Metaiodobenzylguanidine in Chronic Chagas Cardiomyopathy", The Journal of Nuclear Medicine, 52(4): 504-510, Apr. 2011.

* cited by examiner

DETECTION OF REDUCED-CONTROL CARDIAC ZONES

RELATED APPLICATIONS

This application is a continuation of U.S. patent application Ser. No. 14/917,285, filed on Mar. 8, 2016, which is a National Phase of PCT Patent Application No. PCT/M2014/064316 having International Filing Date of Sep. 8, 2014, which claims the benefit of priority under 35 USC § 119(e) of:

U.S. Provisional Patent Application No. 61/875,069 filed Sep. 8, 2013, U.S. Provisional Patent Application No. 61/875,070 filed Sep. 8, 2013, U.S. Provisional Patent Application No. 61/875,074 filed Sep. 8, 2013, U.S. Provisional Patent Application No. 61/925,670 filed Jan. 10, 2014, U.S. Provisional Patent Application No. 61/925,669 filed Jan. 10, 2014, U.S. Provisional Patent Application No. 62/003,108 filed May 27, 2014, U.S. Provisional Patent Application No. 62/030,740 filed Jul. 30, 2014, U.S. Provisional Patent Application No. 62/030,972 filed Jul. 30, 2014, and U.S. Provisional Patent Application No. 62/030,917 filed Jul. 30, 2014.

PCT Patent Application No. PCT/IB2014/064316 is also a Continuation-in-Part (CIP) of PCT Patent Application No. PCT/IL2014/050086 filed Jan. 24, 2014, PCT Patent Application No. PCT/IL2014/050088 filed Jan. 24, 2014, PCT Patent Application No. PCT/IL2014/050089 filed Jan. 24, 2014, PCT Patent Application No. PCT/IL2014/050090 filed Jan. 24, 2014, and PCT Patent Application No. PCT/IL2014/050246 filed Mar. 11, 2014.

The contents of the above applications are incorporated by reference as if fully set forth herein in their entirety.

FIELD AND BACKGROUND OF THE INVENTION

The present invention, in some embodiments thereof, relates to detection of tissue with reduced and/or mismatched innervation, and more particularly, but not exclusively, to detecting viable cardiac tissue that lacks nervous control.

SUMMARY OF THE INVENTION

There is provided in accordance with an exemplary embodiment of the invention, a method of treating cardiac arrhythmia in a heart, comprising: (i) determining that cardiac tissue is viable but with reduced innervation; and (ii) ablating the tissue to reduce a prevalence of arrhythmia in said heart.

Optionally, said determining comprises detecting portions of heart wall which lack electrical activity. Optionally or alternatively, determining comprises determining a zone having a minimal dimension smaller than 20 mm. Optionally or alternatively, determining comprises determining a zone having a length of at least 50 mm. Optionally or alternatively, ablating comprises ablating near regions of a heart wall where muscle died. Optionally or alternatively, ablating comprises ablating a boundary region between tissue with normal and tissue with reduced innervation. Optionally or alternatively, ablating comprises ablating less than 50% of tissue determined to have reduced innervation while being viable. Optionally or alternatively, the method comprises aligning said determined reduced innervation tissue with electrophysiological data. Optionally or alternatively, the method comprises correlating said determined reduced innervation tissue with one or both of the identification of arrhythmic foci and identification of reentrant loop, and ablating based on a result of said correlating. Optionally or alternatively, the method comprises generating an image of a portion of said heart delineating said tissue that is viable and with reduced innervation. Optionally, said image has a resolution of better than 5 mm. Optionally or alternatively, said image has at least three levels of innervation shown. Optionally or alternatively, generating the image comprises using dual isotope radioimaging. Optionally, said radioimaging comprises using a model of the wall of the heart to reconstruct emissions collected form said isotopes. Optionally or alternatively, said dual isotope imaging comprises reconstructing an image of viability using one tracer and reconstructing an image of nervous control using a second tracer and determining a mismatch between the two images. Optionally or alternatively, said dual isotopes comprise Tc-99 and I-131 or I-123.

In an exemplary embodiment of the invention, generating an image comprises comparing an image indicating viability or tissue type with an image indication of nervous control.

In an exemplary embodiment of the invention, the method comprises displaying said image to a physician.

In an exemplary embodiment of the invention, said determining comprises determining using electrophysiological measurements.

There is provided in accordance with an exemplary embodiment of the invention a method of cardiac mapping comprising: (i) identifying portions of the heart with reduced nervous control; and (ii) arranging said portions in a map.

Optionally, the method comprises identifying portions of the heart that are viable and portions of the heart that are not viable. Optionally or alternatively, the method comprises identifying portions of the heart muscle which are hibernating, with at least some electrical activity but no mechanical activity. Optionally or alternatively, the method comprises identifying portions of said heart with reduced ganglion control. Optionally or alternatively, the method comprises diagnosing a heart ailment based on said map. Optionally, said diagnosing comprises identifying portion of said heart at risk for causing or maintaining arrhythmia.

In an exemplary embodiment of the invention, the method comprises treating said heart based on said map. Optionally, said treating comprises ablating at least part of said identified portions with reduced nervous control. Optionally or alternatively, said treating comprises selecting a pharmaceutical regimen based on said map. Optionally or alternatively, said treating comprises selecting a pacing location or a pacing type based on said map. Optionally or alternatively, identifying comprises dual isotope radio imaging.

There is provided in accordance with an exemplary embodiment of the invention a map showing portions of a heart wall that are mechanically active but have reduced nervous control, stored on a non-volatile computer storage media.

There is provided in accordance with an exemplary embodiment of the invention apparatus for carrying out the method described herein.

There is provided in accordance with an exemplary embodiment of the invention apparatus comprising circuitry configured to compare a viability image with a nervous control image and generate a map of portions with viability and reduced nervous control.

There is provided in accordance with an exemplary embodiment of the invention a method of detecting or diagnosing a pathology due to unbalanced damage and/or functioning of body tissue, comprising: (i) measuring the distribution of functionality of a first affected function; (ii) measuring the distribution of functionality of a second affected function; and (iii) identifying areas of unbalanced damage.

Optionally, said measuring comprises measuring using a nuclear medicine imager to detect differences in functionality within regions smaller than 900×900×900 mm in volume, smaller than 600×600×600 mm in volume, smaller than 300×300×300 mm in volume, smaller than 70×70×70 mm in volume, smaller than 50×50×50 mm in volume, smaller than 20×20×20 mm in volume, smaller than 10×10×10 mm in volume, and/or intermediate or larger volumes. Optionally, the volume of the functional region itself is smaller than 70×70×70 mm in volume, smaller than 50×50×50 mm in volume, smaller than 20×20×20 mm in volume, smaller than 10×10×10 mm in volume, and/or intermediate or larger volumes.

According to an aspect of some embodiments of the present invention, there is provided a method of treating organ dysfunction due to autonomic innervation mismatch, comprising: (i) determining that tissue of an organ is viable but with reduced innervation; and (ii) ablating body tissue to reduce a prevalence of the dysfunction in the organ.

According to some embodiments of the invention, determining comprises determining a zone having a minimal dimension smaller than 20 mm.

According to some embodiments of the present invention, there is provided a method wherein determining comprises determining a zone having a length of at least 50 mm.

According to some embodiments of the present invention, there is provided a method wherein ablating comprises ablating a boundary region between tissue with normal and tissue with reduced innervation.

According to some embodiments of the present invention, there is provided a method wherein ablating comprises ablating less than 50% of tissue determined to have reduced innervation while being viable.

According to some embodiments of the present invention, there is provided a method comprising aligning the determined reduced innervation tissue with electrophysiological data.

According to some embodiments of the present invention, there is provided a method comprising generating an image of a portion of the organ delineating the tissue that is viable and with reduced innervation.

According to some embodiments of the invention, the image has a resolution of better than 5 mm.

According to some embodiments of the invention, the image has at least three levels of innervation shown.

According to some embodiments of the invention, generating the image comprises using dual isotope radioimaging.

According to some embodiments of the invention, the radioimaging comprises using a model of the anatomy of the organ to reconstruct emissions collected from the isotopes.

According to some embodiments of the invention, the dual isotope imaging comprises reconstructing an image of viability using one tracer and reconstructing an image of nervous control using a second tracer and determining a mismatch between the two images.

According to some embodiments of the invention, the dual isotopes comprise Tc-99 and I-131 or I-123.

According to some embodiments of the invention, generating an image comprises comparing an image indicating viability or tissue type with an image indication of nervous control.

According to some embodiments of the present invention, there is provided a method comprising displaying the image to a physician.

According to some embodiments of the present invention, there is provided a method wherein the determining comprises determining using electrophysiological measurements.

According to some embodiments of the present invention, there is provided the method wherein the organ is a heart, and the dysfunction is arrhythmia.

According to some embodiments of the invention, the body tissue comprises cardiac tissue.

According to some embodiments of the invention, the cardiac tissue comprises a portion of the viable but reduced-innervation cardiac tissue.

According to some embodiments of the invention, the body tissue comprises non-cardiac tissue.

According to some embodiments of the invention, the body tissue comprises neural tissue.

According to some embodiments of the invention, the determining comprises detecting portions of heart wall which lack electrical activity.

According to some embodiments of the invention, ablating comprises ablating near regions of a heart wall where muscle died.

According to some embodiments of the present invention, there is provided a method comprising correlating the determined reduced innervation tissue with one or both of the identification of arrhythmic foci and identification of reentrant loop, and ablating based on a result of the correlating.

According to an aspect of some embodiments of the present invention, there is provided a method of organ mapping comprising: (i) identifying portions of the organ with reduced nervous control; and (ii) arranging the portions in a map.

According to some embodiments of the present invention, there is provided a method according to claim 25, also comprising identifying portions of the organ that are viable and portions of the organ that are not viable.

According to some embodiments of the present invention, there is provided a method comprising identifying portions of the organ with reduced ganglion control.

According to some embodiments of the present invention, there is provided a method comprising diagnosing an illness of the organ based on the map.

According to some embodiments of the invention, the diagnosing comprises identifying portion of the organ at risk for causing or maintaining a functional disorder. According to some embodiments of the present invention, there is provided a method comprising treating the organ based on the map.

According to some embodiments of the invention, the treating comprises ablating at least part of a portion of the organ with reduced nervous control.

According to some embodiments of the invention, the treating comprises selecting a pharmaceutical regimen based on the map.

According to some embodiments of the invention, identifying comprises dual isotope radio imaging.

According to some embodiments of the invention, the organ is a heart.

According to some embodiments of the present invention, there is provided a method comprising identifying portions of the heart muscle which are hibernating, with at least some electrical activity but no mechanical activity.

According to some embodiments of the invention, the organ is a heart, and the diagnosing comprises identifying portion of the heart at risk for causing or maintaining arrhythmia.

According to some embodiments of the invention, the organ is a heart, and the treating comprises selecting a pacing location or a pacing type based on the map.

According to an aspect of some embodiments of the present invention, there is provided a map showing portions of a heart wall that are mechanically active but have reduced nervous control, stored on a non-volatile computer storage media.

According to an aspect of some embodiments of the present invention, there is provided a map showing portions of an organ anatomy that are functionally active but have reduced nervous control, stored on a non-volatile computer storage media.

According to an aspect of some embodiments of the present invention, there is provided apparatus for carrying out the method.

According to an aspect of some embodiments of the present invention, there is provided apparatus comprising circuitry configured to compare a viability image with a nervous control image and generate a map of portions with viability and reduced nervous control.

According to an aspect of some embodiments of the present invention, there is provided a method of detecting or diagnosing a pathology due to unbalanced damage and/or functioning of body tissue, comprising: (i) measuring the distribution of functionality of a first affected function; (ii) measuring the distribution of functionality of a second affected function; and (iii) identifying areas of unbalanced damage.

According to some embodiments of the invention, the measuring comprises measuring using a nuclear medicine imager to detect differences in functionality in regions smaller than 20×20×20 millimeters in volume.

According to an aspect of some embodiments of the present invention, there is provided a method of treating cardiac arrhythmia in a heart, comprising: (i) determining an imbalance between cardiac tissue innervation and viability; and (ii) ablating tissue to change the balance between innervation and viability to reduce prevalence of arrhythmia in the heart.

According to some embodiments of the invention, the determining an imbalance comprises determining a potential mode of arrhythmic contraction within a region of imbalance between cardiac tissue innervation and viability.

According to some embodiments of the invention, the changing of the balance comprises ablation of tissue within a region of participating in the potential mode of arrhythmic contraction.

According to an aspect of some embodiments of the present invention, there is provided a system for treating dysfunction of an organ, comprising: a modeling unit, configured to receive functional image data of the organ and determine therefrom a model describing: regions of organ viability, and regions of reduced organ innervation; a treatment planning unit, configured to: match the model with a disease-treatment template, according to a disease condition modeled in the template, and provide a treatment plan associated with the template, according to the match.

According to some embodiments of the invention, the treatment plan comprises an indication selecting a portion of body tissue for ablation.

According to some embodiments of the invention, the organ is a heart, and the dysfunction is arrhythmia.

According to some embodiments of the invention, the body tissue comprises cardiac tissue.

According to some embodiments of the invention, the cardiac tissue comprises a portion of the viable but reduced-innervation cardiac tissue.

According to some embodiments of the invention, the body tissue comprises non-cardiac tissue.

According to some embodiments of the invention, the body tissue comprises neural tissue.

According to some embodiments of the invention, the modeled disease condition comprises an indication of potential arrhythmia.

According to some embodiments of the invention, the organ is an organ of the gastrointestinal tract.

According to some embodiments of the invention, the organ is the stomach.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
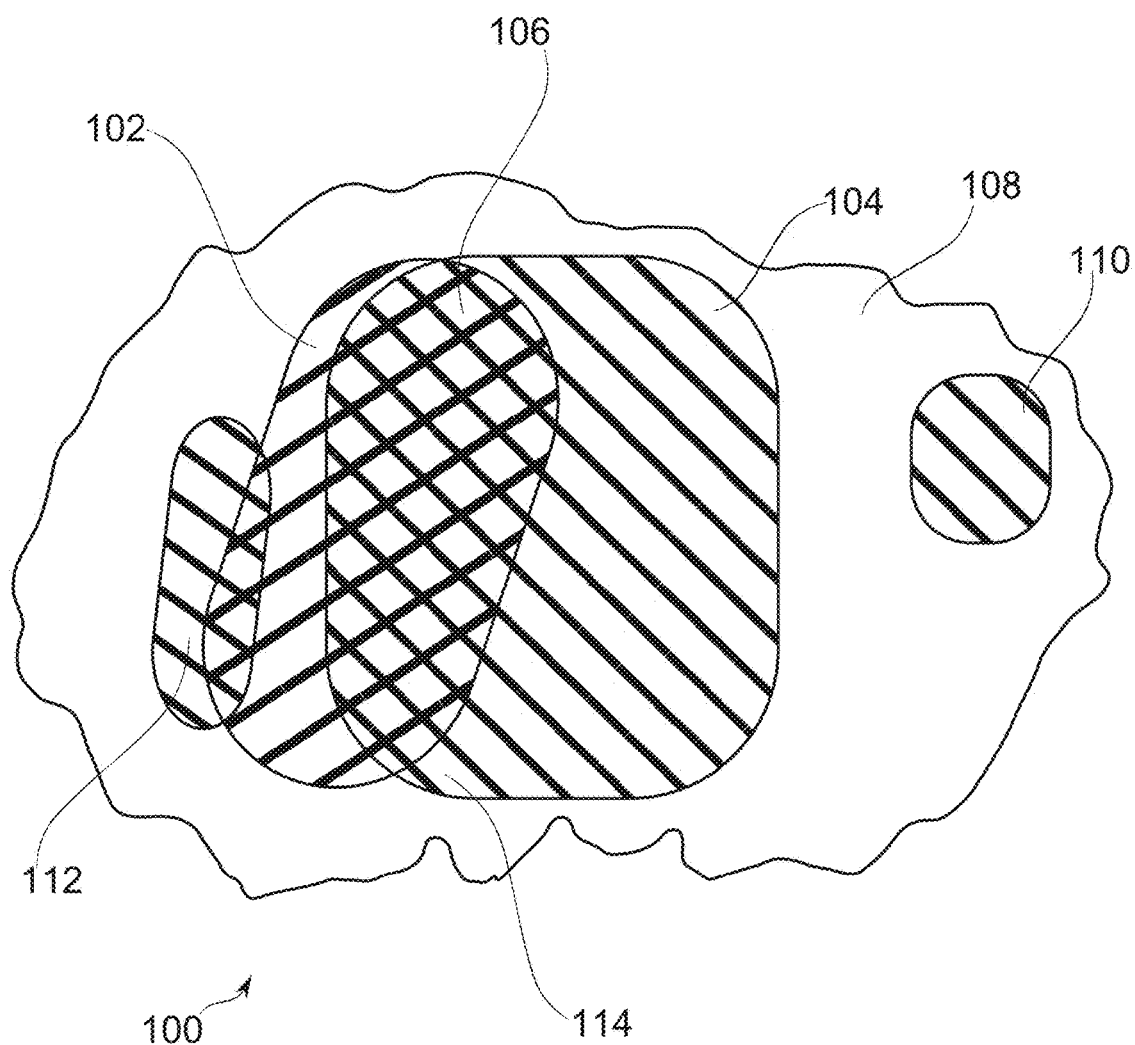
FIG. 1 is a schematic showing of cardiac tissue including dead zones, living zones hibernating zones and zones with reduced nervous control.

The present invention, in some embodiments thereof, relates to detection of tissue with reduced and/or mismatched innervation, and more particularly, but not exclusively, to detecting viable cardiac tissue that lacks nervous control.

Overview

A broad aspect of some embodiments of the invention relates to imaging of tissue in a plurality of aspects comprising aspects related to tissue functioning. In some embodiments, two, three, four or more functional aspects are imaged or otherwise measured. In some embodiments, the functional aspects are registered to one another in a map, such that the map, in some respects, may be said to "image the pathology" of a diseased organ.

A broad aspect of some embodiments of the invention relates to tissue with a mismatch among a plurality of functional aspects such as innervation and viability; for example: tissue with damaged innervation and intact (or less damaged) viability and/or tissue with damaged viability but intact (or less damaged) innervation. In some embodiments of the invention matching and/or mismatching among multiple functional aspects of a tissue is related to, the functional aspects including, for example, innervation, viability, ischemia, contractility, perfusion, metabolism, and/or another function aspect of tissue. In some embodiments a plurality of functional aspects is related to, for example, two, three, four, five, six, seven, or more functional aspects. In some embodiments of the invention, function is measured, for example, by nuclear imaging of the uptake of a radiolabel, the uptake of which is proportional to a functional aspect such as metabolism, innervation, and/or viability. In some embodiments, a measurement of blood flow volume is converted to a measure of, for example, ischemia or perfusion. In some embodiments, dynamic imaging such as fluoroscopy is used to determine contractility. In some embodiments, another imaging modality is used, optionally together with a tag or tracer suitable for indicating a particular functional aspect of the tissue.

Some embodiments of the invention relate to cardiac tissue, but other embodiments are used in other tissue types. In general, in an exemplary embodiment of the invention, the spatial properties of areas with reduced innervation are compared with those of areas with reduced viability. Non-overlapping areas and/or boundaries between such areas and/or with healthy (and/or balanced) tissue may be especially problematic. For example, in the heart, boundary areas are hypothesized to generate and/or maintain arrhythmia.

In an exemplary embodiment of the invention, diagnosis and/or treatment plan is based on the idea that areas with mismatched viability and innervation tend to respond differently than matched tissue to demands on the tissue. The differences may be, for example, in a time profile of a response to demand or differences in an amplitude profile of a response to demand. In electrically excitable tissue, such difference can increase susceptibility to arrhythmia. In contractile tissue, such imbalances may give rise to induction of ischemia due to imbalance between oxygen/nutrients supply and the local metabolic demand. In contractile structure such imbalances can generate an uncoordinated type of heart contraction increasing inefficiency in propelling the blood out of a heart chamber. Potentially, uncoordinated contraction can lead to progressively poorer perfusion of the heart and increasingly uncoordinated contraction (for example, as a result of ischemia). Potentially, this feedback cycle can end in death of an individual. In healthy and/or some matched tissues, when the response of different parts is different, the nervous control system (and/or another body system) acts to coordinate the work and/or balance the responses. However, in mismatched tissue, such balancing may be faulty and lead to various pathologies such as arrhythmia, high stress, ischemia, inefficient metabolism, uncoordinated motion and/or inefficient contraction.

In an exemplary embodiment of the invention, such mismatch detection is used to assess the effect of diffuse illnesses, such as nerve damage caused by diabetes (e.g., or other causes such as storage diseases, degenerative diseases and hypertension). In such an example, in an exemplary embodiment of the invention, tissue (e.g., cardiac or otherwise) is imaged with two tracers, one for detecting nerve activity and one for detecting tissue functionality (e.g., metabolism). Areas of mismatch are optionally flagged as potentially problem causing and/or to be the target of treatment and/or monitoring. In the case of gastric paresis due to diabetes, a possible finding (for which investigative imaging and/or processing may be performed) will be that the synaptic activity of the autonomic nervous system is (e.g., uniformly) decreased in certain conditions while the local motility is also further decreased (match); however, in certain cases, the gastric activity (e.g., motility) is under reduced control of the autonomic nervous system and irregular and/or spatially non-uniform motility activity appears. In another example, a mismatch between gastric (and/or other GI) contract activity and gastric (and/or other GI) digestion secretion appears.

An aspect of some embodiments of the invention relates to the effect of unbalanced damage to body tissue, where such unbalanced (or mismatched) damage relates to the selective damage of a first tissue component, relative to that of a different tissue component. Optionally, damage to a tissue component comprises a functional aspect, for example, due to loss of innervation. In an exemplary embodiment of the invention, one component is a working component and/or function and the other component is a control component and/or function. In other examples, the two components are both of working type and/or both of control type. One example is mismatched damage to nerve and muscle tissue. Another example is mismatched damage to different nerve types (e.g., sensing and control nerves or efferent and efferent nerves, respectively). In an exemplary embodiment of the invention, by providing high resolution functional imaging, the fact of such selective damage can be determined and/or visualized. In an additional example, the two tissue functions are kidney glomerular function and kidney hormonal sensitivity. Optionally, function is measured, for example, by the deposit, washout, and/or uptake of a radiolabeled marker that passes through the glomerulus. Optionally, hormonal sensitivity is measured, for example, by imaging of hormonal receptor binding, where a radiolabeled hormone analog is bound.

In a more general example of some embodiments of the invention, one component of tissue function is from a first group and a second from a second group. For example, group I contains and is not limited to, muscle cell, fibrous tissue, endocrine tissue, exocrine tissue, skeletal tissue, connective tissue, neural tissue, parenchymal tissue of the liver, spleen, kidney, glomerular tissue of the kidney, and/or acinar tissue of the salivary glands. For example, group II includes but is not limited to muscle cell, fibrous tissue, endocrine tissue, exocrine tissue, skeletal tissue, connective tissue, neural tissue, parenchymal tissue of the liver, spleen, kidney, glomerular tissue of the kidney, and/or acinar tissue of the salivary glands.

In an exemplary embodiment of the invention, one or more of mapping, quantifying, diagnosing, planning to treat, and/or treatment or treatment guidance for a pathology is based on the ability to map multitude of function in a region and the understanding that normal conditions relate to balanced function of all tissue components. Identification of the unbalanced (e.g., unmatched) situation, can enable the physician or the technician to map, quantify, diagnose, plan a treatment and/or guide a treatment for a multitude of disease processes. It is particularly noted that control mechanisms, such as nervous control, can serve to balance otherwise unbalanced function. Often lack of balanced behavior is due to or includes a component of nervous damage.

It is noted that while the description has focused on unbalancing of two components, unbalancing as detected and/or treated in accordance with some embodiments of the invention can be in three or more dimensions as well. Such multidimensional balance (or lack thereof) is the general balance of a multitude of functions. In a healthy tissue, all functions are balanced (or can be balanced under suitable control) with all other functions through the entire space of allowable and/or possible range. For example, body temperature, liver metabolism, renal function and heart function are all time varying. In healthy tissue these variations are coordinated and compensate for each other so that together a homeostasis is preserved. In a disease condition, an imbalance can cause failure of the homeostasis and/or require overwork by on e or more components leading to a disorder. In an exemplary embodiment of the invention, such balance and/or lack of balance is detected by imaging, optionally over time, and searching for mismatches. Optionally or alternatively, such balance or lack of balance is detected by taking data about tissue activity and searching for mismatching, for example mismatch in spatial areas of behavior and/or mismatch in temporal response between areas and/or between physiological mechanisms.

Other examples of disordered and/or mismatched timing comprise patients with certain forms of CNS disorder (Parkinson's disease, for example, or depression). The ANS is potentially significant in controlling the conduction velocity, refractoriness, excitability and/or sustaining of brain circuits. Some modes of circuit control, when present, potentially underlie, for example, disturbed behavior or mood: for example, depression (in relation, for example, to the limbic system) or a disease such as Parkinson's syndrome (in relation, for example, to motor control). Potentially, ANS system modulation impinging on the CNS affects activity in such regions, and therefore influences the propagation of electrical impulses in the brain. Damage to the control ANS system potentially comprises a lesion in some part of the ganglia and/or nerve fibers controlling the brain. This condition can lead, for example, to the creation of a spatial dispersion (differences among regions) in the electrophysiology of the brain. Such anisotropy in turn potentially comprises a substrate within which new (possibly pathological) circuit activity patterns arise.

A propagating message can get lost in an area of such a pattern, for example, due to circuit noise, altered conduction velocity, increased likelihood of encountering a refractory circuit element, or another reason.

Unbalanced damage to tissue components can arise from multiple reasons including, but not limited to:

Different sensitivity of each component to a same chemical, viral, pathogen stimuli.

The fact that certain tissue components are merely "cables" that are pass through a host tissue undergoing damage. These "cables" tissue components can include, for example, nerves, vessels, tendons, fibers and/or lymphatic channels.

The fact that certain information is conveyed to and from a tissue that is damaged and the information generation/transmission is affected too. However, the effect of the generated/transmitted information is located in region other than those of the affected tissue, potentially giving rise to an unbalanced effect of a single pathological event.

Different pathologies which occur at different times to nearby tissues.

As noted, a particular example is where afferent neural pathways are affected differently than other tissue components co located with them. For example, in the case of the heart: one can find (e.g., due to a process of ischemia, such as a heart attack) the formation of a fibrous tissue replacing the normal contractile tissue (myocytes) of the heart, and the same process and/or the same fibrous response may also disrupt neurons of the autonomic nervous system that traverse the affected area of the heart. These neurons are usually of two types—efferent and afferent neurons, one or both of which may be damaged and/or damaged in an unbalanced manner. This differentiation is based, at least in part, on the direction of messaging of these neuron and/or type of neurotransmitter found at tips thereof and/or existence of receptors (e.g., mechanoreceptors) therein. The afferent neurons convey information from sensors within the tissue (e.g., distal to the damaged area) and the efferent neurons bring messages from areas that are proximal to the damaged area. In some embodiments of the invention, what is expected and/or detected and/or planned for is an upstream damage to the afferent neural system and/or a downstream damage to the efferent system.

In some embodiments of the invention, a plurality of functions of an organ system operate in different states of mutual balance or unbalance through different portions of their operating range. Optionally, a targeted scope of concern for functional balance (with respect to diagnosis and/or treatment) is confined to a sub-portion of this operating range. Optionally, this sub-portion reflects a diseased state. For example, due to a disease process, neural conduction within a certain part of the neural system is changed such that while operating in a low conduction velocity regime, it is matched to the refractory period. However, while operating in a fast conduction velocity regime, matching to the refractory period is lost, and two functions (for example, stimulation and excitability) become unmatched.

Some examples shown below use imaging of sympathetic synapses and show the effect of such lesions. It is noted that based on anatomical knowledge regarding nerves and lesions, upstream and/or downstream nervous damage is optionally estimated.

An aspect of some embodiments of the invention relates to detecting and/or treating a heart with zones having reduced nervous control, especially such zones that border with zones having normal nervous control. In some cases, what is detected and/or treated are zones with a greater mismatch between viability and innervation that other zones and/or borders between the two. In an exemplary embodiment of the invention, such border and/or mismatched zones are suspected as acting as sources of arrhythmia, possibly due to a large dispersion of electrophysiological properties therein. Optionally, such zones are identified and then ablated, for example to prevent and/or treat arrhythmia and/or to reduce its prevalence.

Some embodiments of the invention are based on the realization that cardiac muscle tissue is controlled using several mechanisms, including nervous control, hormonal control and effect of excitation by nearby tissue. In diseased tissue it has now been realized that control may be compromised. Moreover, tissue with compromised control may lie side by side with tissue with normal or less compromised control. This can cause various pathologies. In one example, tissue with reduced nervous control does not react immediately when the heart changes workload, leading to a reduced cardiac output and to significant differences in action potential shape. For example, some tissue may be refractory while nearby tissue is not. Furthermore, the inventors have discovered that such tissue with compromised control and/or borders thereof may be band shaped, which allows it to act as an alternative conduction pathway or reentrant conduction pathway for ventricular (or other) arrhythmia. In another example, noting that a typical stress response starts with nervous control and continues with hormonal control, the same tissue which did not react sufficiently to increased cardiac workload will react or overreact to increased blood levels of hormones (e.g., adrenaline). Such increased response may come, for example, because the compromised tissue cannot have the hormonal effects modulated (e.g., reduced) by nervous control and/or because such tissue may be overly sensitive to hormonal control as a compensation for lack of nervous control.

As can be appreciated, tissue with comprised control may affect cardiac output, cardiac activation profile and stress distribution and/or mediate arrhythmia.

In an exemplary embodiment of the invention, identification of such reduced control zones uses dual isotope radioimaging, with one isotope being used to identify metabolic activity and a second isotope used to identify the activity of presynaptic neurons and/or the density of receptors for neurotransmitters and/or number of nerve endings. Zones where there is metabolic activity but reduced activity of presynaptic neurons may be considered to have reduced control. It should be noted that a zone may have partial nervous control or no nervous control, as well as full nervous control. In addition, there may be some variability in level of control between parts of the heart. Optionally, also ganglions connected to the heart tissue are imaged and the level of activity therein is used. In some embodiments, the level of activity helps determine the "driving force" behind the organ. In some embodiments, the level of activity is used to correct for an assumption of the effect of density of receptors. For example, a highly active ganglion may compensate for lower density of nerve endings and vice versa (lack of ganglion activity may indicate substantially inoperative nerve endings).

In some embodiments of the invention, the image identifies areas at the border between innervation and the denervation tissue of the heart, which areas may be prone to having a large dispersion of electrophysiological (and/or electromechanical) properties, for example, those that are usually under autonomic nervous modulation.

In an exemplary embodiment of the invention, a patient is treated, for example, by ablating problematic zones. Optionally or alternatively, long conduction pathways are ablated to split them. Optionally or alternatively, when pacing, pacing locations are selected according to the degree of tissue control. For example, anti-arrhythmic pacing may be selected to be in a reduced control zone. Optionally or alternatively, drug treatment (e.g., beta blockers) may be selected according to an expected amount of tissue control. Optionally, ablation is of a cardiac ganglion residing at a higher level than a problematic ganglion. Potentially, ablation of a higher-level ganglion act to homogenize input to an overall region, such that it is less vulnerable to entering a mode of mismatched activity. It should be noted that this potentially comprises a sacrifice of some level of control, in order to avoid the occurrence of a worse condition, such as an arrhythmia.

Denervation ablation, in some embodiments, comprises, for example, ablation of innervation along blood vessels. Optionally, ablation is along wall surfaces (inner or outer) of less than, for example, $1\times1$ mm$^2$, $3\times3$ mm$^2$, $6\times6$ mm$^2$, $15\times15$ mm$^2$, $40\times40$ mm$^2$, $80\times80$ mm$^2$, or another greater, lesser, or intermediate surface size. Optionally, ablation is within a volume of less than, for example, $1\times1\times1$ mm$^3$, $3\times3\times3$ mm$^3$, $8\times8\times8$ mm$^3$, $20\times20\times20$ mm$^3$, $40\times40\times40$ mm$^3$, or another greater, lesser, or intermediate volume size. Ablation is, for example, in the organ to be treated, to another organ which has an effect carried to the organ requiring treatment by a neural pathway, and/or to another organ which has an effect carried to the organ requiring treatment by a non-neural pathway.

In some cases, treatment may be selected even without imaging. For example, having identified that reduced control tissue may be a cause of an arrhythmia, in a patient where arrhythmia is triggered by stress or stopping of stress, ablation of cardiac tissue surrounding electrically dead zones may be carried out, even without identifying such zones as lacking nervous control. For example, if there is a large infarct area, a plurality of point ablations may be carried out along its circumference, so as to break up conduction pathways in reduced control tissue, which may be located therein.

It is noted that in some cases the portion of the heart which is not viable may be small or non-existent. Thus, a heart may include areas with reduced nervous control and not have nearby areas with reduced viability. A possible treatment for such areas is to ablate them so as to avoid a mismatch between control and viability.

Another possible treatment for such areas (e.g., where areas that are under control are adjacent to areas that are not under control; innervated adjacent to denervated areas) is as follows. In such areas, the existence of possible dispersion of properties can bring about a significant complication (for example in the case of electrical conducting tissue that is exposed to sympathetic stimuli, the innervated tissue will have a faster conduction velocity and a shorter refractory period instantaneously with the arrival of the neural input; however, the denervated tissue will not change its electrophysiological properties as the direct sympathetic innervations is disrupted (denervated). The danger of this situation is the appurtenant spatial dispersion of electrophysiological properties which is a potential cause for the formation of reentrant arrhythmias. A treatment in this case can be the formation (e.g., by ablation) of a boundary line between the innervated and the denervated regions such that electrical signal will not be able to propagate from one section to the adjacent section. Additionally or alternatively, administration of a drug, for example one known in the art to have conduction velocity effects, potentially changes conduction velocity, for example, reducing it by up to 50%. Potentially, the reduction in speed alters the timing of events in the tissue such that a threshold for entering a dangerous mode of operation (for example, arrhythmia), is raised.

It is noted that while this description is focused on the heart, as it is an important organ, other organs may be imaged and/or treated as well, for example, the stomach, which can also include zones which are viable and are lacking sufficient nervous control.

Before explaining at least one embodiment of the invention in detail, it is to be understood that the invention is not necessarily limited in its application to the details of construction and the arrangement of the components and/or methods set forth in the following description and/or illustrated in the drawings and/or given in the Examples. The invention is capable of other embodiments or of being practiced or carried out in various ways.

Referring now to the drawings, FIG. 1 is a schematic showing cardiac tissue 100 including dead zones, living zones, hibernating zones and zones with reduced nervous control. In the example shown, an infarct area 102 is dead and is substantially fibrous tissue (e.g., after healing). An area 104 indicates a portion which has reduced or no nervous control. An area 106 shows an overlap between areas 104 and 102 where tissue is not viable and also has no nervous control. Generally, dead tissue 102 will not be able to have nervous control. However, in some cases, nerves serving the area may be viable (e.g., the serving ganglions are viable) and if the dead tissue recovers and/or is treated to recover, such tissue may or may not have nervous control.

An area 108 indicates healthy tissue. An area 110 indicates tissue which is mechanically and/or electrically healthy, but which lacks (or has reduced) nervous control and/or which has more damage to the nervous control mechanism than to its organic function. This process of selective impairment of different co-located tissues is the hallmark of certain disease processes such as diabetes, storage disease, vascular, neoplastic, toxic materials, infectious disease, and many other disease states. The underlying cause may be the selective damage to nerve tissue and/or damage to nerve fibers in one location which cause impaired nervous control in another.

It is noted that also the opposite type of mismatch may be of interest, tissue with a greater reduced viability than nervous control.

In these disease processes, the susceptibility of a component of a tissue to the pathophysiologic process of the disease is often highly variable although all components are co-located. For example, in diabetes is it well known that neural tissue is more sensitive than other tissues to the microvascular damage caused by long-standing diabetes. Furthermore, the specific neural damage of diabetes is further more specific in sub-group of nerves that have a much higher sensitivity to diabetes damage (at times a threefold higher sensitivity). For example, in a long standing diabetic patient one may find preservation of most of the peripheral neuronal function with a very specific damage to nerves conducting vibration information, or to nerves conducting temperature information.

Specific damage to very specific tissue components can also be seen in other diseases, such as viral diseases (or autoimmune responses thereto), which can, for example, affect specific neurons in specific centers of the brain (for example in the visual cortex, or in the auditory canal).

In some cases, the disease-specific damage to specific tissue components can be further sub-divided by location. This type of behavior may explain very discrete loss of function of one component as compared to (or in addition to) the generalized loss of function in other disease pathology (for example blunt trauma). Such an area may act as a focus for imbalanced control of bodily system.

In an exemplary embodiment of the invention, the etiology of such diseases and/or potential consequences and/or treatment is determined by imaging to determine unbalanced regions and/or their relationship to balanced regions and/or the effect of such regions and/or boundaries thereof on systemic function of organs and/or the body.

An area 112 indicates an elongate section with reduced nervous control near and/or overlapping area 102 which is substantially dead. As noted herein, such an area may act as a reentry circuit for certain types of arrhythmia.

An area 114 indicates a hibernating region, which is damaged by ischemia and so lacks mechanical activity and possibly some measure of electrical activity, but may also lack some or all nervous control. Even if not a danger at a current time, as such tissue recovers danger may occur.

In an exemplary embodiment of the invention, the size of the damaged areas and/or mismatch areas is relatively small, for example, being between 10×10 mm and 100×100 mm, and/or, for example, between 10×10 and 50×50 mm. Optionally, a maximal extent of such a region is less than 70 mm, 50 mm, 30 mm or 20 mm. In some embodiments, however, smaller mismatched regions are detected, for example, between 1×1 mm and 10×10 mm in extent. Areas larger than 100×100 mm may also be detected.

In an exemplary embodiment of the invention, the distance between the centers of the areas is between 10 and 100 mm. In some embodiments, the areas are a patchwork of interleaved areas, which may be, for example, between 10×10 and 200×200 mm in size. Such a patchwork may include, for example, between 2 and 20 areas; for example, 3, 5, 6, 8 or an intermediate or greater number of areas with mismatched viability and nervous control.

While FIG. 1 shows a plan view of muscle tissue 100, it is noted that dead zones and zones with reduced nervous control may occur at different depths of tissue. So a same-tissue location may have one layer with viability and nervous control, a second layer with viability but no nervous control, a third layer with nervous control (e.g., if colonized by stem cells) but no viability and/or a fourth layer with neither viability nor nervous control.

It is also noted that some parts of the heart may have intermediate levels of nervous control rather than just binary levels.

Figure 2:
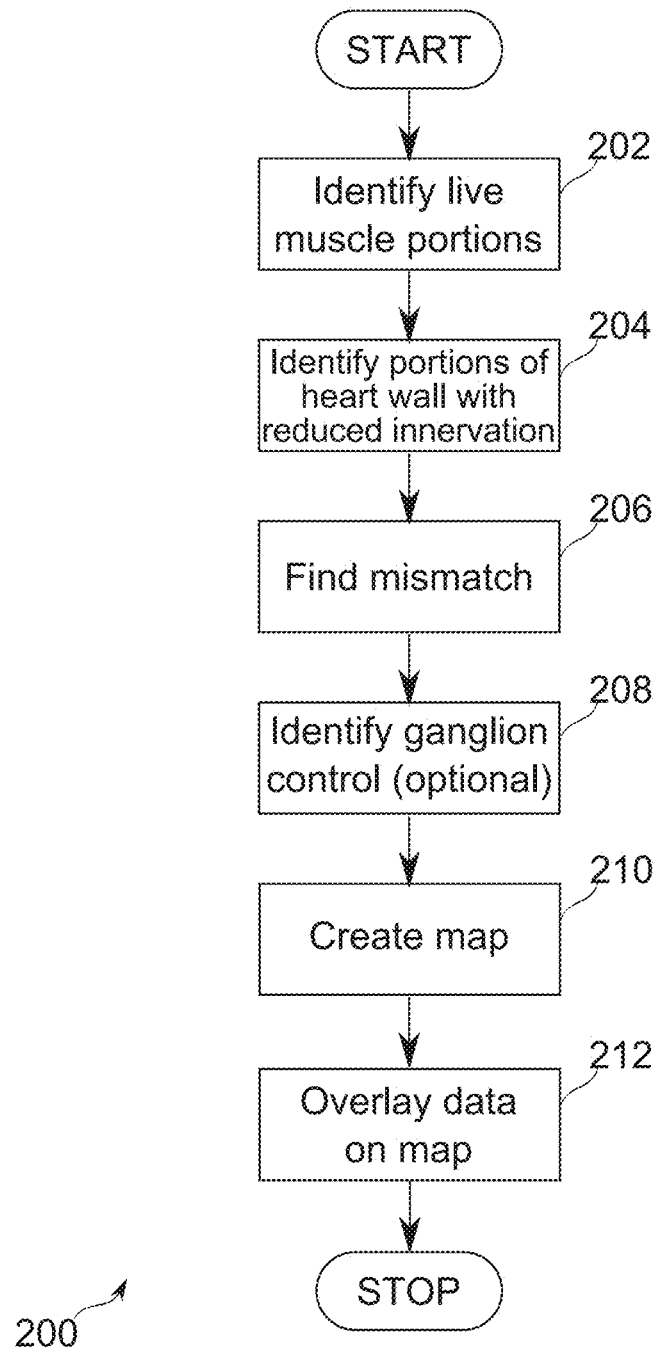
FIG. 2 is a flowchart of a method of identifying cardiac tissue zones with reduced nervous control, in accordance with some exemplary embodiments of the invention.

FIG. 2 is a flowchart 200 of a method of identifying cardiac tissue zones with reduced nervous control, in accordance with some exemplary embodiments of the invention.

Figure 3A:
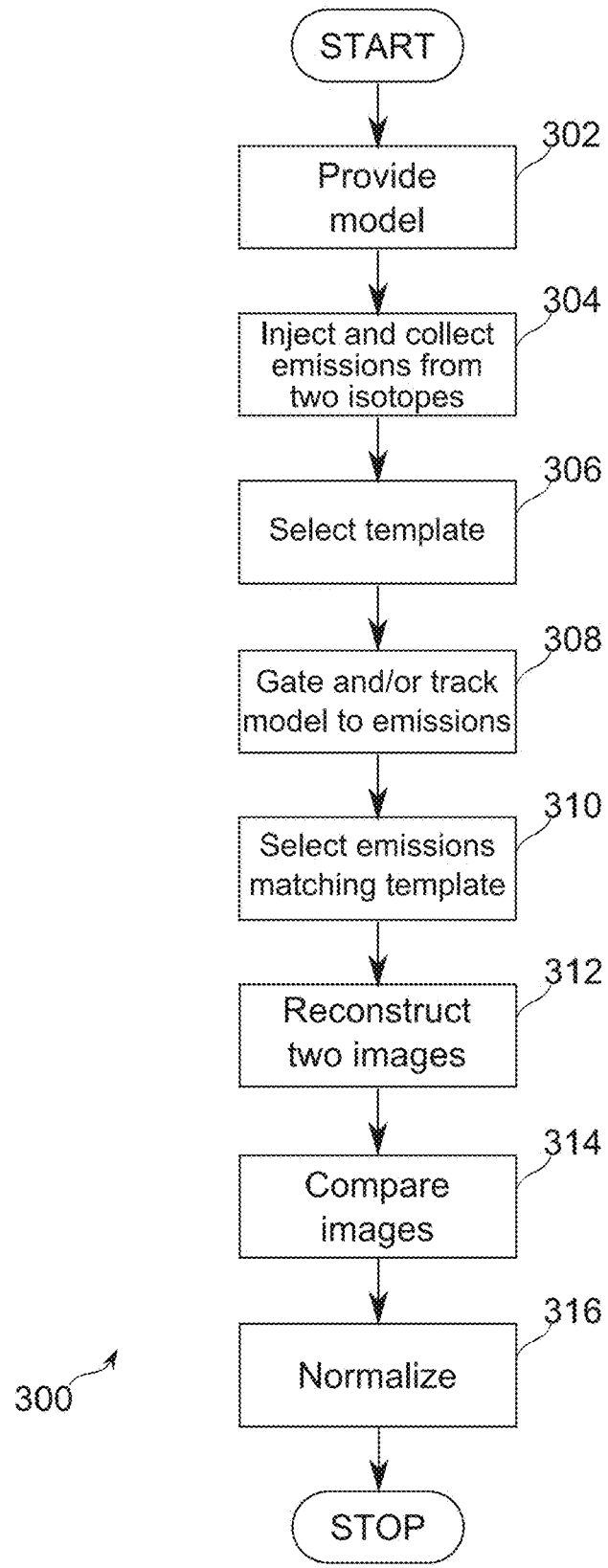
FIG. 3A is a flowchart of a method of radioimaging to find cardiac zones with reduced control, in accordance with some exemplary embodiments of the invention.

At 202, live portions of muscle are detected, for example, using radioimaging techniques (e.g., FIG. 3A).

At 204, portions of heart wall with reduced innervation are detected, for example by detecting a level of innervation and identifying areas with a low such level. Optionally, radioimaging techniques (e.g., FIG. 3A) are used for such detecting.

At 206, a mismatch between non-viable areas and non-controlled areas is determined, for example, by correlating and/or otherwise comparing a map of viability and a map of nervous control.

In some embodiments of the invention, nervous control is further determined by mapping ganglions that control the muscle 208. Optionally, the level of activity in a ganglion is used to compensate for a perceived level of nervous control.

While, in general, nervous control is not binary, it is further noted that for various reasons the amount of nervous control at different parts of the heart may be different and/or may be detected as being different. Optionally, a map indicating allowed ranges for each portion of the heart is used to determine if a detected difference is a real difference or within normal parameters. Optionally, comparison to a previously acquired map of the patient is used. Optionally or alternatively, a heart-wide threshold (sharp or fuzzy) method is used to indicate lack or reduced or normal control levels.

It is noted that the viability of different parts of the heart may vary, especially imaging thereof may vary. As described for control, a map or threshold may be provided for viability determination.

Optionally, as described below, acquired data are normalized.

At 210, a map of the heart is generated indicating areas with a mismatch between nervous control potential (and/or activity) and viability. Optionally, a plurality of levels of control is indicated, for example, 2, 3, 4, 5, 10, or smaller, intermediate, or greater number of levels of control. Optionally or alternatively, a plurality of levels of viability is indicated, for example, 2, 3, 4, 5, 10, or smaller, intermediate, or greater number of levels of viability. In some embodiments, only types of areas are shown and/or overlaid on the map; for example, "normal", "dead" and "live but uncontrolled". Optionally, other data, for example, relating to ischemia, are shown as well. Optionally, such data are used to assess the risk of a location reacting inappropriately to excitation and/or stress and/or nervous control and/or hormonal control and/or load on heart and/or a treatment.

Optionally, at 212, various data, such as EP (electrophysiology) data are overlaid on the map. An example of such EP data includes areas that are suspected of being arrhythmia reentrant circuits and/or arrhythmia foci.

In an exemplary embodiment of the invention, the map is a high resolution map, for example with a resolution of better than 5 millimeters, 3 millimeters, and/or 2 millimeters. Optionally or alternatively, the map discriminates between different layers in the cardiac muscle wall. Optionally, the wall mapped is a ventricular wall, for example, the left ventricle. Optionally or alternatively, the wall is an atrial wall, for example, of the left atrium or the right atrium.

In an exemplary embodiment of the invention, the detected reduced control viable regions are non-blob shaped and/or include non-blob regions. For example, a blob may be an area which can enclose a 20 mm×20 mm or 30 mm×30 mm circle and may be generally convex. In contrast, the detected areas may be, for example, elongate or arc shaped, for example with a length:width ratio of at least 1:5, 1:10, or more.

FIG. 3A is a flowchart 300 of a method of radioimaging data processing, in accordance with some exemplary embodiments of the invention, which uses a model of the heart to localize radiation emissions to heart walls and then determine uncontrolled viable tissue therein. While in some embodiments of the invention, the method shown in U.S. Patent Application Publication No. 2009/0201291, the disclosure of which is incorporated herein by reference, is used for image reconstruction; in others, a different method, for example the following method, may be used. In any case, it is noted that in some embodiments, the method comprises substantially acts 312-314: reconstructing two images and comparing them. The images may be provided in various ways, for example, as described below.

At 302 a model of the heart is provided. Such a model is optionally generated using a CT imager. In an exemplary embodiment of the invention, the model is a 4-D model which includes different shapes for different parts of the cardiac cycle.

At 304, radioactive emissions are collected from the body. This may be done, for example, before, during and/or after model provision. Optionally, the data acquisition is binned or gated according to cardiac cycle (e.g., using an ECG sensor to indicate state in cycle). In an exemplary embodiment of the invention, emissions are generated by first injecting the patient with two tracers, one which is selectively taken up by viable tissue (e.g., Tc-99 in Sestamibi) and one which is selectively taken up by nerve endings or tissue which collects adrenaline (e.g., mIBG with I-123 or I-131).

At block 306, a template for reconstructing the heart wall is selected and/or otherwise generated. Block 306 may be carried out before, during and/or after data collection. In an exemplary embodiment of the invention, the template is an oversize template, for example, redefining the wall thickness to be a factor of between 1.1 and 2 of the thickness indicated in the model. In an exemplary embodiment of the invention, this factor is a function of the thickness of an imaged (e.g., reconstructed nuclear image) portion of the heart. For example, the template thickness of the left ventricle is set to be a factor of about 1.2 of the thickness of the left ventricle. Optionally or alternatively, the thickness of the right ventricle wall is set to be a factor of about 0.7. Factors of about 0.5 are optionally used for the atrial walls. It is noted that these factors are generally oversize with respect to the true wall thickness.

In an exemplary embodiment of the invention, the template is generated by defining a first shape which fits inside the model and defining a second shape which encloses the model and defining the template (walls of interest) as lying between the two shapes.

At block 308, a correspondence between the template and the emission data are provided. For example, such a correspondence may be 3-D or 4-D. Optionally, the template is resized and registered to match the apparent size of the heart. Optionally, this resizing uses one or more landmarks in the heart, for example, the left ventricle, which are acquired by reconstructing an image of the heart using the acquired emission data. Optionally or alternatively, other registration cues are used, for example, the right ventricle, the liver or torso. Optionally or alternatively, an iterative reconstruction process is used with an initial guess for the template registration being provided (e.g., manually) and then the reconstruction is repeated to converge on the template.

In one example, an average image (average between diastole and systole) is computed and used for registration.

In one example, the image (and/or model) of the heart is manually segmented, for example, to indicate the left atrium.

At 310, emissions from locations that match the template are collected and used to reconstruct one or two images. If the template is 4-D, a 4-D image is optionally reconstructed. Optionally, for analysis, a series of images of the heart are integrated—for example, averaged—with the model being used to define a mapping between different parts of the images at different times.

At 312, two separate images are reconstructed, one for viability and one for nervous control. Alternatively, a single image is reconstructed, with different tracers being tagged differently in the same image. A potential advantage of first reconstructing one image and then two images, is that the combined data may be more plentiful and may be used to more accurately reconstruct the shape of the heart. Then, the data may be separated into two images and/or layers on an image.

In some embodiments, one or both of the images are previously acquired. For example, in some cases a CT image, MRI image, and/or fluoroscopy image may be used to provide a viability image, optionally also acting as a basis for a model as described above. Optionally or alternatively, an image of fiber zones (for example, acquired as described in U.S. Provisional Patent Application No. 61/925,669 filed Jan. 10, 2014 titled "DETECTION OF SCAR AND FIBROUS CARDIAC ZONES"), is used as a viability image.

At 314 the two images are compared and analyzed, for example, to generate indications of sections which are both viable and not sufficiently controlled.

At 316, the values of the image(s) are optionally normalized along a scale between maximum and minimum. A threshold is optionally defined (e.g., 15%), below which an area is assumed to be non-active and/or not suitably controlled. Optionally, different thresholds are provided for different parts of the heart and/or based on a mapping of ganglionic activity.

Optionally, in the image, the wall thicknesses are corrected according to an average wall thickness. It is noted that some parts of the heart may be reconstructed so that a muscle wall thickness spans only a single voxel. In some cases, the identification of problematic zones is includes also a depth coordinate relative to the wall surfaces e.g., near inner surface, near outer surface, in mid area, spanning surface).

Various data may be overlaid on the reconstructed image, for example, data from the model or data from other imaging modalities. In particular, electrical measurement data may be overlaid and images of implants may be overlaid.

Figure 3B:
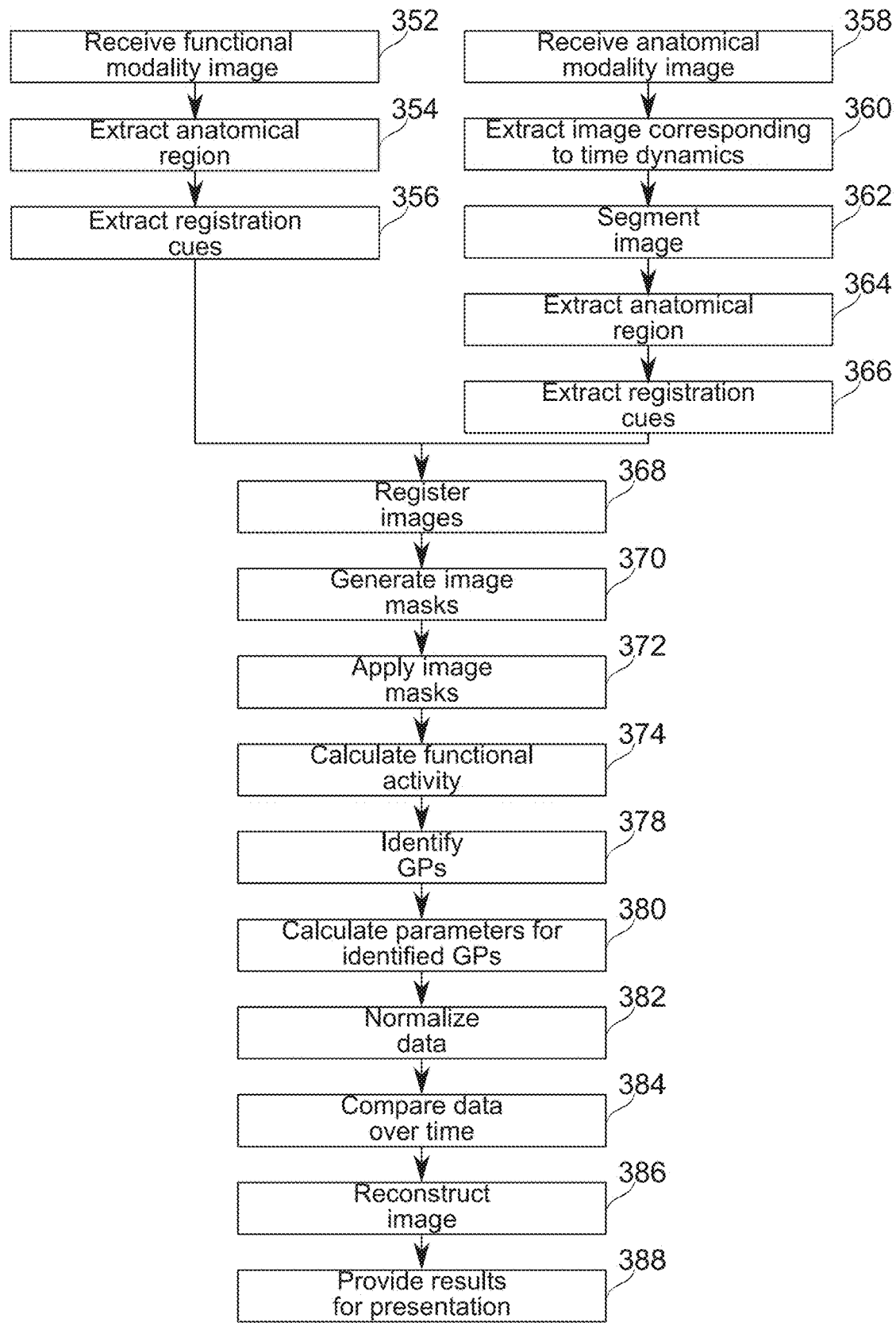
FIG. 3B is a flow chart of a method for processing functional images to identify and/or locate one or more ANS components (such as ganglia), according to some exemplary embodiments of the invention.

Reference is now made to FIG. 3B which is a flow chart of a method for processing functional images to identify and/or locate one or more ANS components (such as ganglia), according to some exemplary embodiments of the invention.

A branch of the flowchart of FIG. 3B begins, and in some embodiments of the invention, at block 352, functional imaging modality data and/or images are received.

The data and/or images comprise, for example, a D-SPECT image and/or other images. Received images, in some embodiments, are of a body part; for example: a torso, abdomen, heart, or another body part, according to the scanning protocol selected. The body part, in some embodiments, includes nervous system tissue to be imaged, and/or the innervated organ itself. For example, nerve tissue comprises GPs of the heart, intestines and/or another organ. Optionally, the functional images include regions of activity that denote nerve tissue such as a GP made detectable, for example, by uptake of a radiotracer such as mIBG. In some embodiments, a two tracers are used; for example, first tracer such as mIBG to label activity, and a second tracer to image tissue vitality.

Optionally, functional data is collected from a body part that has regions where nerve activity is expected, and regions where nerve activity is not expected. For example, during imaging of the heart, data denoting nerve activity is expected from the heart wall and/or surrounding tissues, and no nerve activity is expected from inside the blood-filled hollow chambers. Potentially, noise is received from areas corresponding to the inside of the heart chamber, though no true activity is expected. Optionally, the noise is removed from the functional data based on the corresponding anatomical image; for example, after image registration. Optionally, intensity denoting noise within blood- or other fluid-filled chambers and/or vessels is removed. For example, intensity readings of the functional data corresponding to heart chambers and/or surrounding blood vessels are removed by applying one or more image mask on functional image. In some embodiments, fluid-filled chamber noise is used in obtaining a noise estimate applicable to other tissue locations.

In some embodiments of the invention, at block 354, an anatomical region is extracted from the image. Optionally, tissue image regions (potentially containing nerve structures) are segmented from hollow spaces (non-innervated, but potentially containing fluid). For example, the wall of the left ventricle (LV) and/or the hollow space within the LV is extracted. Optionally, the extracted region is a layer of tissue, such as the tissue layers forming the LV wall, instead of, for example, the LV including the hollow chamber inside the LV. In exemplary cases of kidney imaging, the walls of the renal artery are extracted and/or the inside of the artery is extracted. When imaging other organs, dominant portions of the organ are optionally selected.

In some embodiments of the invention, at block 356, one or more registration cues are extracted from the image. Potential sources of registration cues include, for example, the organ of interest, and/or surrounding anatomical structures. Particular examples include the LV axis, liver, heart septum, RV, and/or torso. Optionally, registration cues are used to match anatomical images with functional images, and/or to match anatomical images during a physiological cycle, such as the cardiac cycle.

Another branch of the flowchart of FIG. 3B begins, and in some embodiments of the invention, at block 358, anatomical image modality data and/or images are received. Anatomical image modality data comprises data obtained, for example, from a CT, MRI, 3D ultrasound, 2D ultrasound, fluoroscope, or by another modality. The anatomical image denotes the structure of the tissue and/or organ innervated by nerve tissue, such as a GP. The anatomical image denotes the tissue and/or organ structure corresponding to the location of nerve tissue such as a GP. The anatomical images, in some embodiments, contain both the nerve tissue to be functionally imaged and the innervated organ. Alternatively, anatomical data is received that is not personalized to the patient, for example, from a general anatomical model.

Optionally, anatomical data from an anatomical imaging modality is received to reconstruct an anatomical image of a region of a body of a patient. Optionally, the region comprises a portion of at least one internal body part which borders on a target nerve tissue.

The anatomical images and the functional images denote corresponding regions of the body containing the GPs for identification and/or localization. For example, both modalities are employable to take pictures of the heart, kidney, or other organs. To image GPs of the heart, for example, anatomical and/or functional images of the heart are obtained. To image GPs of the kidney, in another example, anatomical and/or functional images of the kidney, renal artery and/or aorta are obtained.

In some embodiments of the invention, at block 360, images corresponding to different times during a dynamic cycle are optionally extracted and/or acquired. For example, for the heart, images are extracted along the cardiac cycle. Periods selectable along the cardiac cycle for extraction include, for example, the end diastolic volume (EDV) and/or the end systolic volume (ESV). In another example: for the bladder, images are optionally extracted corresponding to a full bladder and an emptying bladder.

In some embodiments, the average image is computed, for example, as (EDV+ESV)/2.

In some embodiments of the invention, at block 362, one or more images are segmented. Segmentation, in some embodiments, is fully automatic. In some embodiments, segmentation requires or potentially involves manual user intervention.

In some embodiments of the invention, at block 364, an anatomical region is extracted. Optionally, the anatomical region corresponds to the anatomical region extracted at block 354. Optionally, the anatomical region is extracted from the segmented image of block 362.

In some embodiments of the invention, at block 366, one or more registration cues are extracted from the image. Potential sources of registration cues include, for example, the organ of interest, and/or surrounding anatomical structures. Particular examples include the LV axis, liver, heart septum, RV, and/or torso.

The branches of the flowchart merge, and in some embodiments of the invention, at block 368, the functional images or data and the anatomical images or data are registered. Optionally, the images are registered based on alignment of the extracted anatomical regions of blocks 354 and 364. Registration is performed manually, automatically and/or semi-automatically.

Optionally, registration takes into account organ dynamics, for example, heart movement. As examples: anatomical images during the dynamic cycle are registered, and/or functional data are corrected for the dynamic movement. As a particular example: intensity readings within the heart chamber are corrected to association with nearby moving heart wall.

In some embodiments of the invention, at block 370, image masks are generated based on the anatomical image and/or data. Optionally, the image masks direct processing and/or visual display of the nerve tissue to specific locations of the image located within the image masks. For example: GPs are displayed and/or processed within the volume of an applied image mask, GPs outside the volume of the image mask are not processed and/or displayed, and/or GPs outside the volume of the image mask are processed and/or displayed differently than those GPs inside the image mask.

Optionally, the anatomical images are processed to generate the image mask corresponding to dimensions of at least one internal body part, for example, the walls of the chambers of the heart. For example, a dimension of an internal body part of the specific patient is calculated and used to define the mask.

Optionally, the image masks are selected and/or defined for tissue surrounding a hollow chamber. As examples, image masks are defined based on:
the shape of the heart chamber walls, excluding the hollow region within the chambers;
the arterial wall, excluding the hollow region within the artery; or
the shape of the bladder, excluding the hollow region within the bladder.

It is noted that nerve structures are potentially confined within the tissues defined by the image masks. The hollow spaces (potentially filled with fluid such as blood, urine or other fluids) are expected to be nerve structure free. Optionally, image masks include tissue surrounding the organ of interest.

The image masks are defined, for example, based on:
image segmentation—such as according to the ability of the system to segment the image;
tissue type—such as muscle vs. connective tissue;
organ size;
structures within the organ—such as heart chambers, liver lobes, or kidney parts;
or another method.

Different image masks are optionally generated for different tissue types, and/or for GPs at different locations within the organ. For example, for each of the GPs within the epicardium and myocardium, a respective set of image masks is generated. Optionally, image masks are generated for fat pads.

The image mask comprises, for example, a 2-D surface and/or 3-D volume with shape and/or size selected based on tissues and/or organ parts within the anatomical image. The image mask optionally corresponds to anatomical parts believed to contain the neural tissue for imaging, such as GPs. For example, the mask corresponds to the: walls of the four heart chambers, intestinal wall, bladder wall, renal artery, aortic branch region of the renal artery, kidney, and/or another structure. In more particular examples, the image mask is generated to contain GPs within the epicardial and/or myocardial tissue of the heart, or kidney innervating GPs at the aorta-renal artery junction.

Optionally, image masks are generated based on an estimated location of the GPs. For example, an estimated location is based on normal patient anatomy, an initial model of the ANS for a patient, and/or known previous ablation or other medical data, such as indications of missing or ablated nervous tissue. Optionally, image masks are generated based on an estimated location of the GPs and dimensions of an internal body part inferred, for example, from an anatomical image. Potentially, this provides an advantage when GPs are not visible on the anatomical image.

Optionally, generated image masks correspond to the segments of the anatomical image. For example, the heart is segmented into chamber walls and the generated image masks correspond to the chamber walls of interest.

In some embodiments of the invention, at block 372, the image masks are applied to the functional image. Alternatively or additionally, the image masks are applied to the functional data. Alternatively or additionally, the image masks are applied to combined functional and anatomical images and/or data, for example, overlaid images.

Optionally, the image masks are applied based on the registration process (block 368). The anatomical information serves as a guide, using the selected image masks, for selective reconstruction of GP related data within the functional image. The image masks may be correlated with the image to contain anatomical structures having the neural tissues. The application may be based on the image registration, for example, applied based on a common coordinate system. The image masks may be applied to a certain type of tissue containing neural tissue. For example, the image masks may be applied to the epicardium of the heart. The image mask may be applied to have its inner surface aligned with the epicardial surface of the chamber wall, such that the image mask contains the epicardial space encompassing the chamber.

Optionally, the generated image mask is correlated with the functional data for guiding the reconstruction of a functional image depicting the target nerve tissue.

In some embodiments of the invention, at block 374, functional activity is calculated within the applied image mask space. Optionally, the average functional activity is calculated. Optionally, the standard deviation of the functional activity is calculated. For the heart example, the functional activity is calculated around each chamber separately, and around the entire heart. Average activity for the chambers may be denoted by A1LV, A1RV, A1LA, and A1RA. Average activity for the heart may be denoted by A1H. Standard deviation of the activity may be denoted by SD1LV, SD1RV, SD1LA, SD1RA, and SD1H. Optionally, average activity and/or standard deviation may be calculated for the entire functional image or data. Optionally, average activity and/or standard deviation is pre-set, e.g., based on previous imaging of the same patient, based on "normal" patient activity etc.

In some embodiments of the invention, at block 378, GPs are identified within the applied image mask space. It should be noted that the term "GP" is used for ease of discussion, and that the method is optionally applied in some embodiments for identifying ANS component(s) or for extracting or identifying other information relating to neural activities, or other tissues. Alternatively or additionally, GPs are identified within the organ volume and/or nearby tissues. Optionally, GPs identified within multiple different image masks that are combined into a single image of all the identified GPs, for example, the identified GPs within the organ. Alternatively or additionally, GPs identified within corresponding image masks of multiple frames over time are combined—such as all image masks of the LV myocardium during the cardiac cycle.

Optionally, areas of extreme activity are identified. For example, epicardial GPs (EGP) and/or myocardial GPs (MGP) are identified based on extreme mIBG activity.

Optionally, GPs are identified based on one or more predefined thresholds and/or rules. Optionally, GPs are identified based on size. Alternatively or additionally, GPs are identified based on activity level in reference to average activity and/or surrounding activity. Alternatively or additionally, GPs are identified based on connectivity between GPs.

In some embodiments, the GP is identified as an object within a particular size constraint. The constraint is, for example, at least about 4×4×4 mm, such as for an EGP; or about 2×2×2 mm, such as for an MGP. Alternatively or additionally, the GP is identified by comparing calculated activity (image intensity) of a certain region to surrounding activity in the same image mask. Alternatively or additionally, the GP is identified by comparing calculated activity within the image mask to activity in another image mask. For example, the EGP is identified as satisfying the rule that the total activity of the EGP is a predefined factor times the standard deviation (SD1 and/or SD2), above average activity (A1 and/or A2), and/or the adjacent activity surrounding it is lower than half of the EGP activity. Optionally, activity is corrected for volume. Optionally, the user selects and/or modifies the predefined factor. For example, the MGP is identified as satisfying the rule that the total activity of the MGP is another predefined factor times the standard deviation (SD1 and/or SD2), above average activity (A1 and/or A2), and/or the adjacent activity surrounding it is lower than half of the MGP activity, optionally corrected for volume. Optionally, the user selects and/or modifies the predefined factor.

Optionally, identification of GPs is performed per frame, optionally per frame of the dynamic cycle (e.g., cardiac cycle).

In some embodiments, the identified GP is automatically related to a tissue type. Optionally, the identified GP is related to the tissue type based on the applied image mask. Alternatively or additionally, the identified GP is related to the tissue type based on the characteristics of the intensity readings. For example, large sizes (denoting large GPs) are potentially only to be found in certain tissues. Optionally, different types of GPs are related to different tissues. For example, myocardial GPs are related to the myocardium and/or epicardial GPs are related to the epicardium.

In some embodiments of the invention, at block 380, one or more parameters are calculated for the identified GPs (also referred to herein as GP parameters). Examples of parameters include:

average size;

specific activity—expressed, for example, in counts per voxel and/or GP/average counts in the corresponding image mask volume;

power spectra—for example, the power below 1 Hz, power between 1-5 Hz, and/or a ratio of high to low frequencies;

normalized power spectra;

GP connectivity map—for example, connectivity and interaction between different GPs; and/or number of GPs per predefined area—expressed, for example, as GP density number/cm$^2$.

For identified EGP, one or more of following parameters is calculated in some embodiments: EGP size, EGP specific activity, EPG power spectra graph, EGP normalized power spectra, and/or a map of EGP connectivity. EGP normalized power spectra are calculated, in some embodiments, as the difference between the EGP power at different frequencies minus the power of the total counts from the myocardial image mask space.

Optionally, calculation of GP parameters is performed per frame, optionally per frame of the dynamic cycle (e.g., cardiac cycle).

In some embodiments of the invention, at block 382, the calculated and/or other parameters are normalized. Normalization optionally takes place at one or more blocks of the method, for example, during and/or after acquiring the functional and/or anatomical images, upon calculation of functional activity, upon identification of GPs, upon calculating parameters for the GP, upon comparison of data over time, or at other blocks.

Examples of normalization techniques include:

raw data;

raw data divided by the raw data value in a known fixed anatomical location acquired at roughly the same time, for example, the activity of the tracer in the patient's mediastinum;

normalization to a normal patient data set;

normalization to a value of the activity at the first or the last image acquisition from a sequence of acquisitions;

normalization to value acquired in different physiological states such as rest/stress;

a combination of some or all of the above; and/or other methods.

Alternatively, normalization is performed instead of and/or in addition to the normalization of block 382 before a different block in the process. For example, normalization is optionally applied before GPs are identified in block 378. Normalization potentially assists identifying the GPs. For example, activity at a local region, such as mIBG activity, is compared to an average value and/or standard deviation across the organ volume, within the image mask space and/or relative to a predefined threshold.

Alternatively or additionally, the calculated data (e.g., blocks 374, 378, 380) and/or measured functional intensity are corrected for sensitivity. Optionally, sensitivity correction is performed within each image mask and/or in related image masks. For example, different areas potentially have relatively higher or lower sensitivity to uptake of the radioagent. Optionally, the anatomical data is correlated to the sensitivity. Optionally, the image masks are generated (block 370) based on different sensitivity levels; for example: one set of image masks for higher sensitivity nerve structures, and another set of image masks for lower sensitivity nerve structures. Optionally, the different sensitivities are normalized to a common baseline.

Alternatively or additionally, measurements of the functional data are normalized. For example, measurements of uptake of the radioagent are normalized to the level of corresponding chemical in the patient. Optionally, intensity measurements are normalized according to the level of activity of GP being identified. Optionally, measurements denoting activity of the GPs are taken. For example, in the case of mIBG, measurements are optionally normalized to the level of norepinephrine (NE), adrenaline and/or epinephrine in the patient. Optionally, the level of NE is measured in the blood, urine, or other body fluids. Intensity of mIBG uptake is normalized based on the measured NE.

Additionally or alternatively, mIBG measurements are normalized to a decay function, such as decay over time since injection of mIBG. In another example, the level of activity is measured by non-chemical methods. For example, normalization of mIBG is performed based on measurements taken during a cardiac stress test. Measurements comprise, for example, ECG measurements, heart rate, cardiac output, and/or other measurements. Optionally, measurements are correlated with levels of activity of the GPs being identified, for example by a table, mathematical equation, or other method.

Additionally or alternatively, measurements of functional data are normalized to a level of one or more electrical properties. For example, functional data are normalized to impulse conduction velocity, refractory period, a measured electrical potential (at one or more phases of contractile state), or another property of the electrical activity of the tissue. Optionally, additional weight is given to regions where conduction is particularly poor: slow to transmit and/or slow to recover, for instance. This is a potential advantage, for example, when evaluating a heart region for severity of disease, and/or for comparing regions for their relative severity of disease.

In some embodiments of the invention, at block 384, data is compared over time. Optionally, changes in GP parameters over time are identified. Optionally, dynamic changes of the calculated parameters between different acquisition times are determined. For example, the changes in GP activity over time are calculated, from injection till 6 hours post injection, by repeating the image acquisition several times during this time window. The functional images are optionally acquired at more than one time after the tracer injection.

In some embodiments of the invention, at block 386, a functional image is reconstructed based on the mask applied to the functional data and/or image. Alternatively or additionally, an image is reconstructed based on the mask applied to the combined functional and anatomical data and/or images. The reconstructed image potentially contains the identified GPs, for example, as regions of increased intensity. The reconstructed image is optionally overlaid on the anatomical image, illustrating the physical location of the GPs.

Alternatively or additionally, the characteristics of the GPs within the functional image are reconstructed. The reconstruction is instructed by the image mask.

In some embodiments of the invention, at block 388, the calculated results from, for example, block 378, 380, 382 and/or 384, and/or reconstructed images (block 386) are provided for presentation or otherwise provided to the operator. They are, for example, presented on a monitor to a physician. Additionally or alternatively, the calculated results and/or reconstructed images are stored in a memory for future use, such as diagnosis. The calculated results potentially assist in diagnosing the patient and/or in guiding treatment.

Optionally, the results are provided for presentation on a certain frame, for example, the end systolic frame. Alternatively, results are provided for presentation on multiple frames, for example, a video of the cardiac cycle.

In some embodiments, the reconstructed functional image or combined functional and anatomical image is provided for registration during a treatment procedure. Optionally, the reconstructed functional image is overlaid on and/or registered with anatomical images obtained during the treatment procedure. Overlaid and/or registered images are optionally used by the operator to physically determine locations of the GPs during the treatment.

The method of FIG. 3B has been described with reference to the heart. The method is not limited to the heart, and is used in some embodiments for other organs, including hollow fluid filled organs such as stomach, aorta, or bladder; and/or solid organs such as kidney or liver. GPs and/or nerve endings are identifiable in these other organs in some embodiments. For example, the aorta is segmented based on surrounding structure such as bones, muscles, and/or branching arteries; and image masks generated accordingly. The liver, in an exemplary embodiment, is segmented based on anatomical liver lobe divisions.

Figure 4:
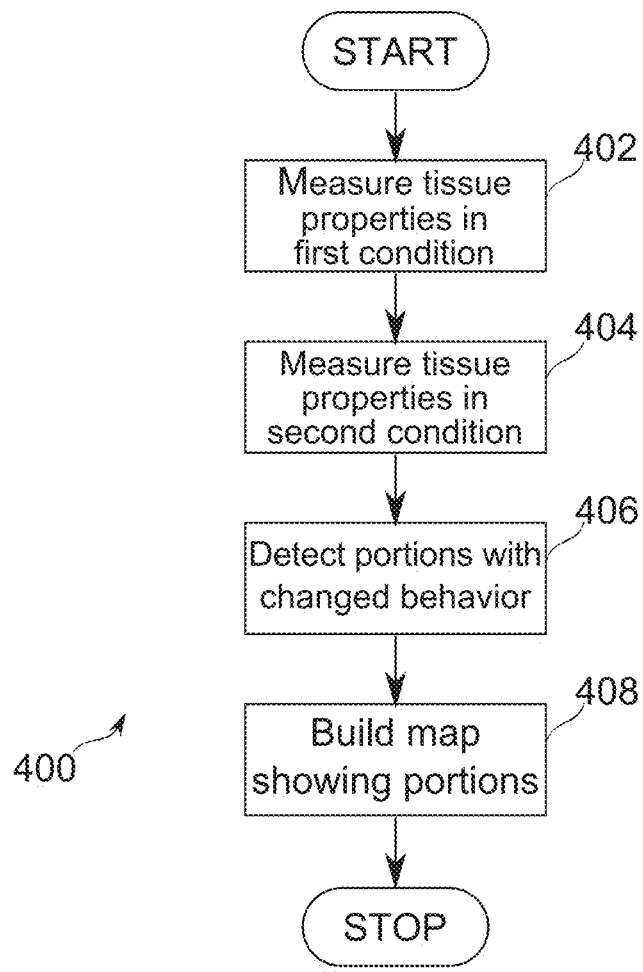
FIG. 4 is a flowchart of a method of finding cardiac zones with reduced control, in accordance with some exemplary embodiments of the invention.

FIG. 4 is a flowchart 400 of a method of finding cardiac zones with reduced control, in accordance with some exemplary embodiments of the invention. As noted above, tissue which has fewer types of control than other tissue is expected to react differently (e.g., mechanically and/or electrically) to changes in cardiac conditions and/or timing of such changes.

At 402 tissue is measured under a first set of conditions, for example, low stress. All tissue (or at least neighboring tissue) may act the same way, for example, exhibiting same conduction velocities, refractory periods, plateau durations and/or other action potential properties. Optionally, the measurement uses an EP catheter system, such as the Biosense-Webster Carto® system.

At 404 the measurement conditions are changed (at least once) and measurement repeated. For example, a greater preload may be applied to heart. Optionally or alternatively, a stress causing agent or exercise may be applied. Optionally or alternatively, a hormone such as adrenaline may be applied. It should be noted that the different conditions may be acute or may be more steady. One example in a change in condition is a sudden recruitment of cardiac output to deal with a stress condition. Another example is after a few seconds or minutes when hormonal levels increase and when, possibly, the stress is reduced so that the nervous system acts to reduce excitability of muscle cells (but insufficiently in muscle segments with reduced nervous control).

At 406 areas with changed behavior are detected. Optionally, only areas near infarct scars are measured, as such areas may be more likely to have the combination of viability and reduced control. Examples of expected changes are changes in EP parameters such as shape of action potential and conduction velocity and changes in mechanical activity, such as contraction strength and/or speed.

While measurement may be using a catheter, in some embodiments, measurement uses radioimaging, for example, single isotope imaging, such as imaging using viability-indicating tracers and/or imaging using nervous control-indicating tracers. Optionally, both imaging and measurement under different conditions are used (e.g., acquiring one-tracer or two-tracer images under various conditions).

At block 408, a map showing the various areas (portions) detected is constructed. Construction is, for example, according to operations described in relation to FIG. 5.

Figure 5:
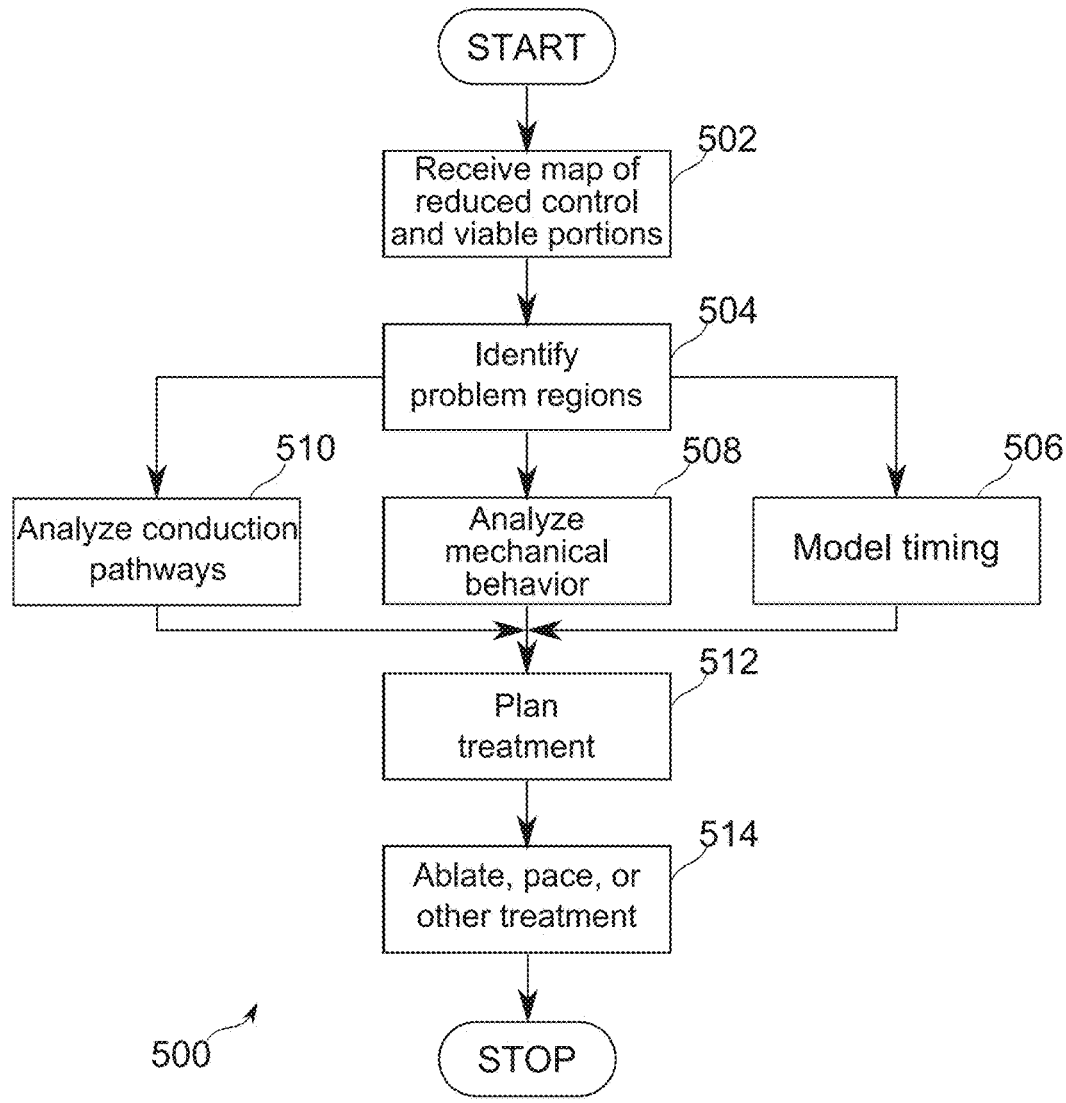
FIG. 5 is a flowchart of a method of reducing cardiac arrhythmia and/or assessing risk and/or diagnosing and/or therapy planning, in accordance with some exemplary embodiments of the invention.

FIG. 5 is a flowchart 500 of a method of reducing cardiac arrhythmia and/or assessing risk and/or diagnosing and/or therapy planning, in accordance with some exemplary embodiments of the invention.

At block 502, a map showing zones with reduced nervous control and/or reduced viability is provided, for example, using methods described herein.

At 504 problematic regions are optionally identified. For example, zones that have a certain size and/or location and combine tissue viability and reduced nervous control, may be identified. In one example, the location is the location of an SA (sinus) node (or other location which acts as a source of the cardiac cycle in a particular patient). Reduced nervous control of the SA node may cause rhythm disturbances, for example, by causing the pacing origin to migrate under different conditions of nervous and/or hormonal activity.

If the provided image is a 4-D image, regions that move over time (e.g., for which amount of control varies with physiological condition) may be identified.

In another example, hibernating or ischemic regions are identified as problematic.

In another example, a tracer with antibodies or other affinity for a hormonal receptor (for example, of a type known in the art) is used to identify regions where hormonal control is unbalanced with other types of control and/or functionality.

Various analyses may be applied to such identified regions. In some embodiments, for example, at 506, the timing of contraction of different parts of the heart may be determined, for example, to assess changes in conduction patterns which increase (or decrease) cardiac output and/or change a risk of aneurysm.

In some embodiments, for example at 508, mechanical behavior of the heart may be analyzed. For example, regions with reduced nervous control may under-contract at some times, over-contract at other times and/or may be ballooned by increased pressure in the heart.

In some embodiments, for example, at 510, conduction pathways may be analyzed. Such analysis can include, for example, an estimation of AF risk (e.g., based on size, shape and/or pattern of reduced control zones and/or reduced viability zones in an atrium). In another example, an estimation of ventricular arrhythmia (e.g., VT) risk is provided, for example, by identifying long conduction pathways (e.g., along reduced control zones). Such analysis may also take into account EP data, for example, which indicates areas with ischemia and/or areas with reduced conduction velocity and/or areas with suspected (e.g., based on ECG) contribution to arrhythmia, such as by acting as foci or as reentry circuits (reentrant loop).

At 512 treatment is planned. The planned treatment, in some embodiments, is for addressing a risk assessed in one of blocks 506-510. Optionally, the treatment is for another purpose. For example, identification of reduced control regions can be used to select an optimal place for a pacemaker lead.

In some embodiments, the analysis of the image is used to interpret EP measurements and/or mechanical measurements (e.g., contraction amount, speed, force and/or change in thickness). For example, a low signal may have different meanings if acquired at a low control region (e.g., any may need to be corrected based on the patient's physiological condition, such as hormonal levels. In addition, the identification of a low control zone can assist in interpreting electrical measurements which are associated with weaker than expected mechanical activity.

In some embodiments, low control zones are used to assess the usefulness and/or desirability of inserting a stent or performing PCTA or other vessel modification. For example, increasing blood flow to a problematic region may increase the chance of an arrhythmia.

In some embodiments, low control zones are used to assess the usefulness of gene therapy or other treatment designed to convert fiber tissue to non-fiber tissue or healing weak tissue (which generally cannot be done for fiber tissue). For example, increasing the amount of uncontrolled tissue in the heart may be undesirable. Conversely, creating a contiguous region of uncontrolled tissue may be desirable in some hearts, and undesirable in others. In another example, rehabilitating tissue may be more desirable if the control infrastructure is available at or near that tissue to be rehabilitated.

In some embodiments, low control zones are used to diagnose a mechanical condition such as HOCM or various cardiomyopathies, such as dilated cardiomyopathies. For example, HOCM may manifest due to uncontrolled tissue failing to contract fast enough and/or soon enough during exercise.

In some embodiments, low control zones are used to assess a risk of cardiac dysfunction due to ischemia or a further infarct and/or assess a prognosis for a patient with heart failure.

It is noted that identification of low control zones, optionally together with information such as viability of tissue, electrical behavior and/or blood flow may be used to diagnose conditions otherwise diagnosed only using biopsy, sometimes after death.

At 514, the heart is optionally treated, for example, by ablation, by vascular manipulation (e.g., stent implantation), heart reshaping apparatus implantation, valve implantation, electrical stimulation, surgery and/or pharmaceuticals.

It is noted that in some cases there is no need to actually detect regions with reduced control. Rather, for example, using the insights described herein, a doctor can diagnose a patient based on symptoms as likely suffering from a condition associated with low control regions (e.g., arrhythmia after exercise and/or at a delay after providing hormonal injection). Optionally, ablation may then be applied near known or identified dead zones in the heart. Optionally, the ablation locations are selected to ensure that conduction pathways through low control tissue, are short enough and/or located at a safe location with respect to other tissue, other dead zones and/or timing of activation in the cardiac cycle.

In an exemplary embodiment of the invention, treatment includes pacing. For example, pacing, such as anti-arrhythmia pacing, may be applied at or near a low control zone, for example, such that the pacing obviates the need for control to avoid arrhythmia or provides arrhythmia control at a location in need thereof. Optionally, pacing is set according to an understanding of the underlying pathology. For example, tissue near a potential re-entrant stimulation loop is paced so that refractory properties of the tissue allow the loop to be blocked from self-propagation. Optionally, pacing is changed in response to conditions likely to lead to an arrhythmia. For example, an increase in heart rate is considered differently, according to how recently and/or how quickly the increase occurred (under neural vs. hormonal control, for example). Optionally, the logic which manages the pacing is contained within a pacemaker, for example, an implanted pacemaker device.

Electrode location may also be an issue for defibrillation, especially defibrillation methods that first attempt to stop fibrillation by capture. Uncontrolled tissue may be easier or more difficult to capture, depending, for example, on the patient, and this may drive electrode placement and/or sensing location. In an exemplary embodiment of the invention, a device for electrical therapy includes a sensor (e.g., and/or is suitable implanted and/or programmed) which is intentionally placed in controlled regions (e.g., to assess a correct activation profile of the heart) and/or in non-controlled regions (e.g., to assess activation of uncontrolled portions of the heart which may have a different refractory period). Optionally, sensing is provided both at controlled and at uncontrolled regions. Optionally, when detecting a large enough divergence between the activities at the two regions, a determination that an arrhythmia is imminent or ongoing is generated.

In another example, pharmaceutical therapy may be selected so as to compensate for the existence of uncontrolled tissue. For example, beta blockers which initially increase tissue sensitivity to hormones and then reduce such sensitivity may be more or less desirable in some patients, for example, based on the pattern, size and/or location of low-control viable regions therein.

In another example, anti-arrhythmia drugs which affect a refractory period may be prescribed based on the detection of low control areas which cause and/or sustain arrhythmia due to a (relatively) shorted refractory period thereof.

In an example of negative treatment, treatment to revive hibernating or ischemic tissue may be avoided if it may increase problem areas.

Figure 6:
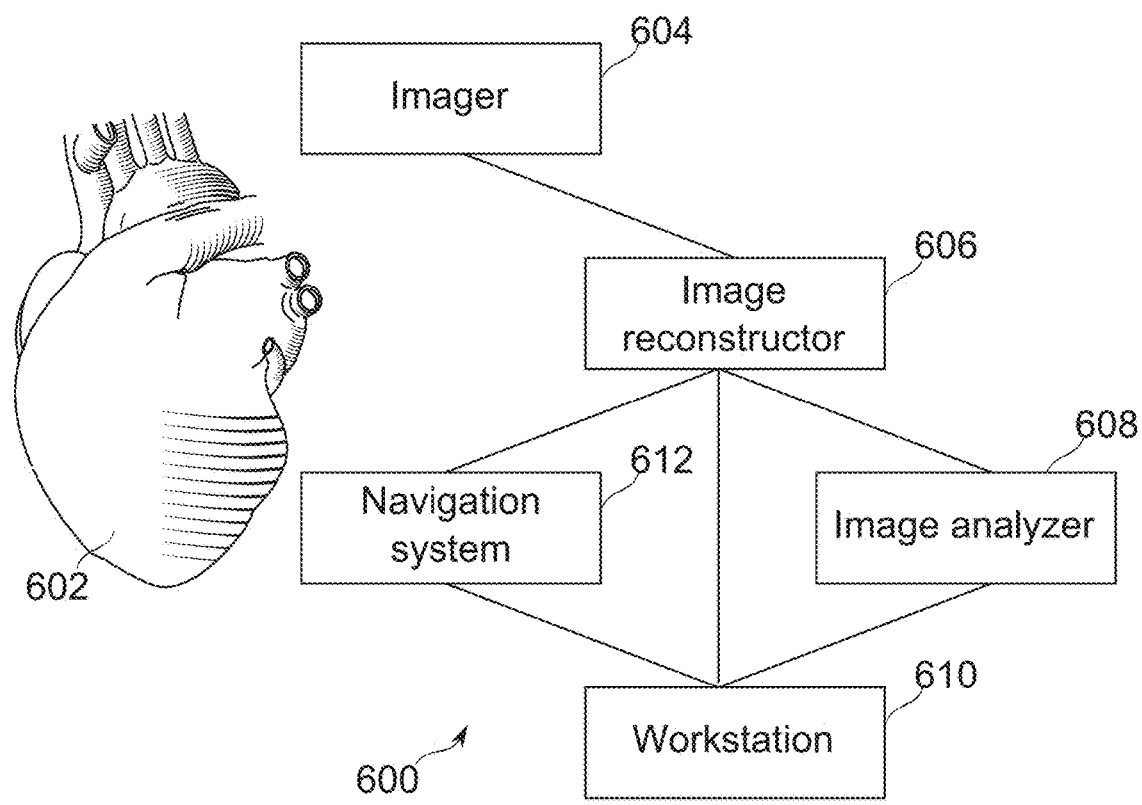
FIG. 6 is a schematic showing of a system for identifying tissue zones with reduced nervous control, in accordance with some exemplary embodiments of the invention.

FIG. 6 is a schematic showing a system 600 for identifying tissue zones with reduced nervous control in a heart 602, in accordance with some exemplary embodiments of the invention.

An imager 604, for example a D-SPECT device as described above is used to acquire information about the heart. Optionally, the imager also acquires a structural image or images to provide a model for the reconstructions. Optionally or alternatively, imager 604 also collects cardiac phase information and/or respiratory phase information. It is noted that such information may also be reconstructed from the acquired data, in some embodiments of the invention.

An image reconstructor 606, optionally bundled with imager 604, but alternatively provided at a remote location, may be used to reconstruct the reduced-control-showing image, for example, as described above.

An image analyzer 608 optionally bundled with one or both of imager 604 and image reconstructor 606 is optionally provided and used to perform automatic and/or semi-automatic analysis of the image, for example, to identify potential arrhythmia sources.

Optionally, a workstation 610 is used to control one or more of imager 604, reconstructor 606 and analyzer 608 and/or to display results generated thereby.

In an exemplary embodiment of the invention, a navigational system 612 is provided which is optionally controlled by work station 610 and which may be loaded with targeting and/or map information provided by the image. In one example, the navigational system 612 comprises a catheter with a position sensor (e.g., the Biosense-Webster Carto® system) and the image is used to guide a procedure performed using the catheter. Such a navigation system 612 may be used with other cath lab equipment such as an X-ray machine. Viability and/or nervous control indications and/or indications of tissue being problematic are optionally overlaid on an image acquired by the X-ray machine. Optionally, registration is provided manually or using the above mentioned position sensor.

In an exemplary embodiment of the invention, the map is used for safety, for example, to indicate to a user that he is about to ablate a viable and well-controlled region, when a nearby region is not well-controlled and may be a better target. Optionally or alternatively, when providing temporary pacing, the system can indicate that pacing is being provided at a location where lack of nervous control interferes with a desired result (or perhaps enhances it).

Figure 7:
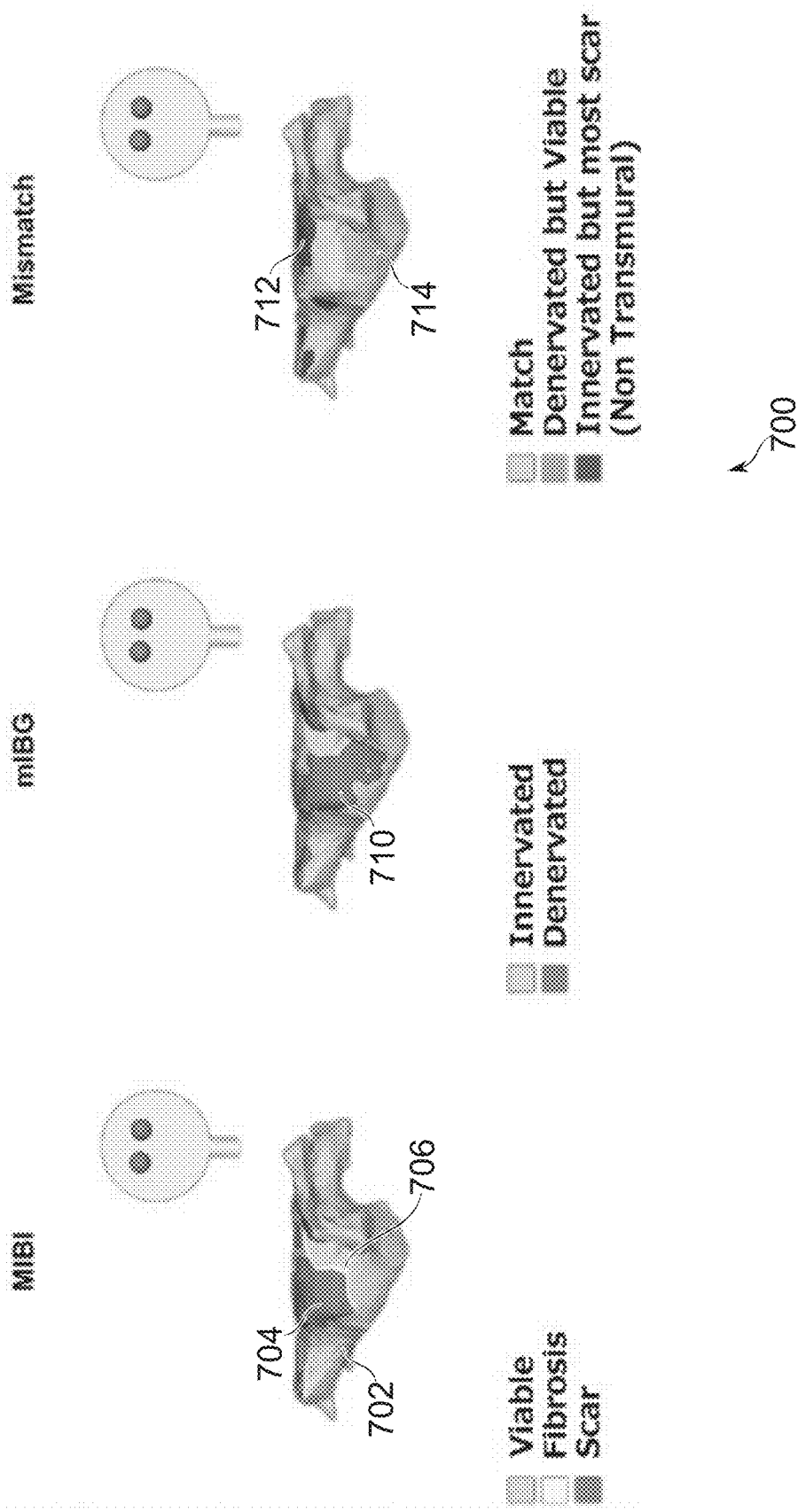
FIG. 7 is a set of nuclear medicine images showing tissue zones with reduced nervous control, in accordance with some exemplary embodiments of the invention.

FIG. 7 is a set 700 of nuclear medicine images showing tissue zones with reduced nervous control, in accordance with some exemplary embodiments of the invention. Shown are three images of a left atrium 702. The left image shows a radioimage reconstructed using a MIBI tracer (e.g., Sestamibi) which indicates viability. Red areas 704 indicate complete scarring/fibrosis and yellow areas 706 (mainly at the border lines in this example) indicate partial fibrosis. In other cases, partial fibrosis has been identified (e.g., using methods of some embodiments of the present invention) in the middle of a supposedly ablated (or otherwise damaged) region. At the top of the image the lack of contiguity of the ablated areas can be seen.

The middle image shows a radioimage reconstructed using a tracer taken up by nerve endings (e.g., mIBG). Reference 710 indicates areas with significantly reduced innervation.

The left figure shows what is already visually apparent, which is the very large mismatch between scarring and denervation. Specifically, an area 712 of innervation and less viable tissue is shown, as is an area 714 of denervated but viable tissue.

Figure 8:
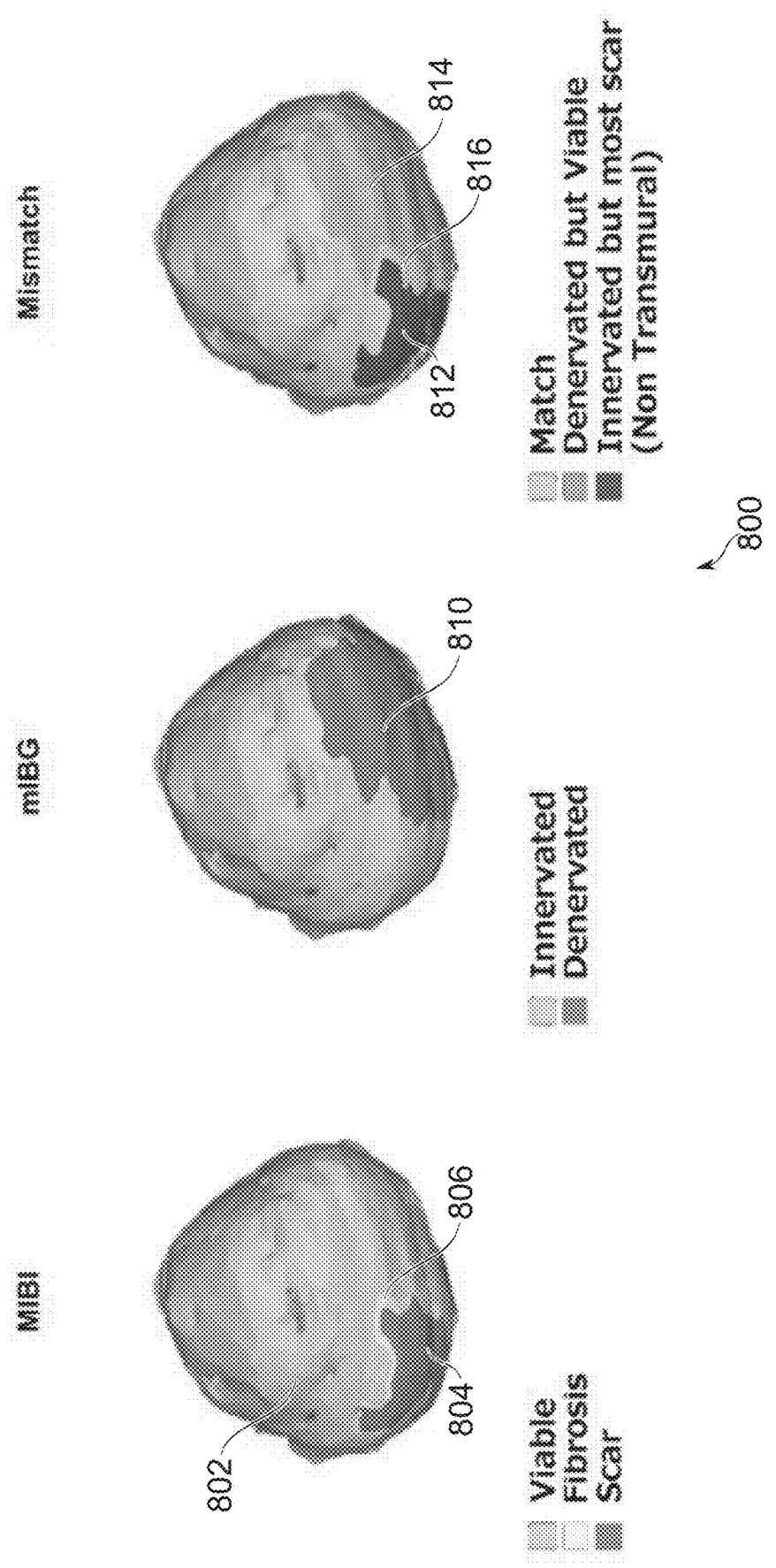
FIG. 8 is a set of nuclear medicine images showing tissue zones with reduced nervous control, in accordance with some exemplary embodiments of the invention.

FIG. 8 is a set 800 of nuclear medicine images showing tissue zones with reduced nervous control, in accordance with some exemplary embodiments of the invention. Shown are three images of a left ventricle 802.

The left image shows a radioimage reconstructed using a MIBI tracer (e.g., Sestamibi) which indicates viability. Red areas 804 indicate complete scarring/fibrosis and yellow areas 806 (mainly at the border lines in this example) indicate partial fibrosis.

The middle image shows a radioimage reconstructed using a tracer taken up by nerve endings (e.g., mIBG). Reference 810 indicates areas with significantly reduced innervation.

The left figure shows what is already visually apparent, which is the very large mismatch between scarring and denervation. Specifically, an area 812 of innervation and less viable tissue is shown, as is an area 814 of denervated but viable tissue. It is noted that the patient suffers from ventricular arrhythmia, caused, it is hypothesized, by the large size and/or boundary of area 814 and/or a gap 816 between the two areas.

Figure 9:
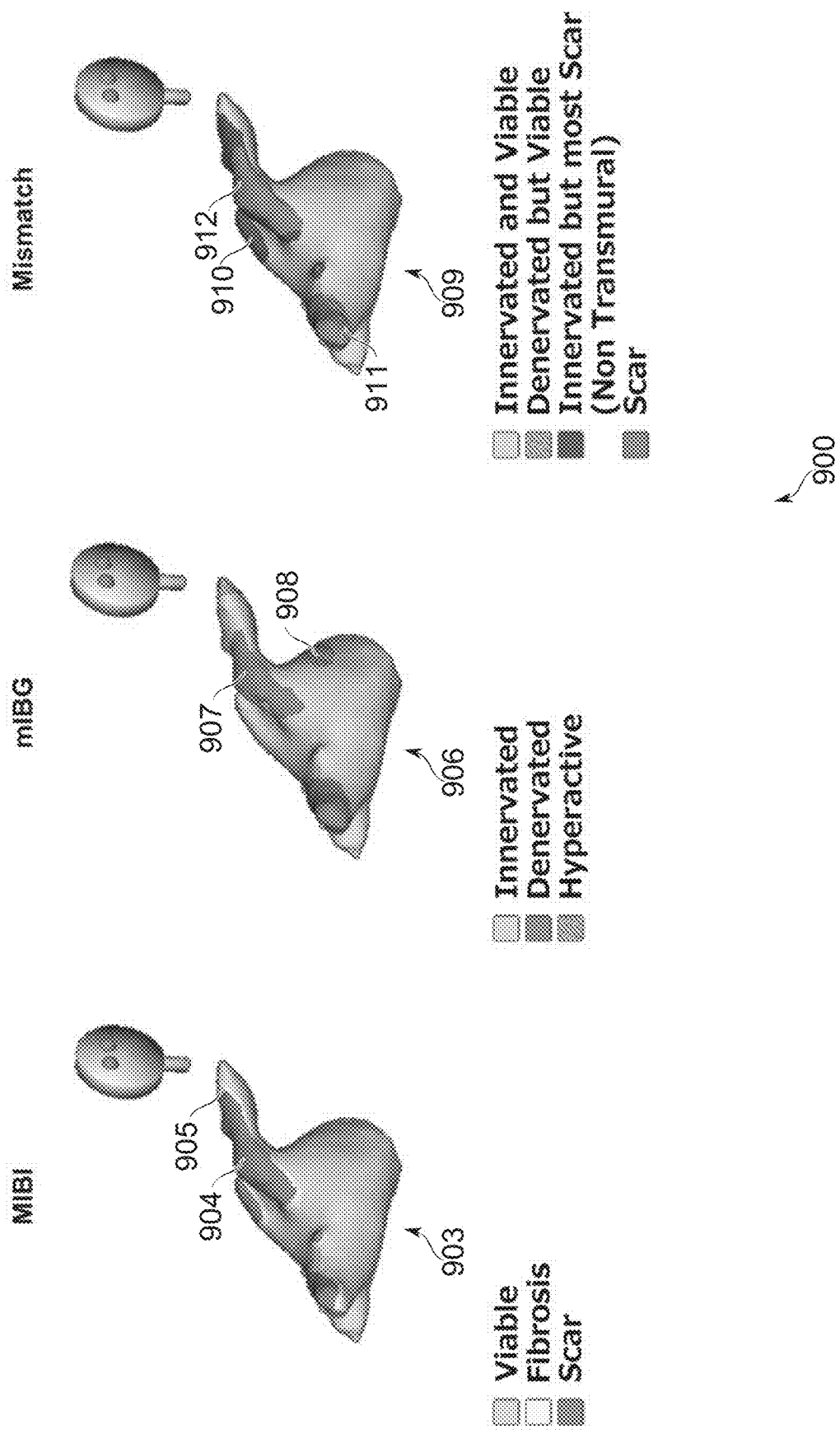
FIG. 9 is a set of nuclear medicine images showing left atrium tissue zones with scarring and/or abnormal nervous control, according to some exemplary embodiments of the invention.

It should be noted that the method of normalization and display used in FIGS. 8-9 emphasizes health/innervation mismatches in particular. Regions of notionally equivalent health and innervation are shown in green in the right-most images whether effectively healthy, or not.

Figure 10:
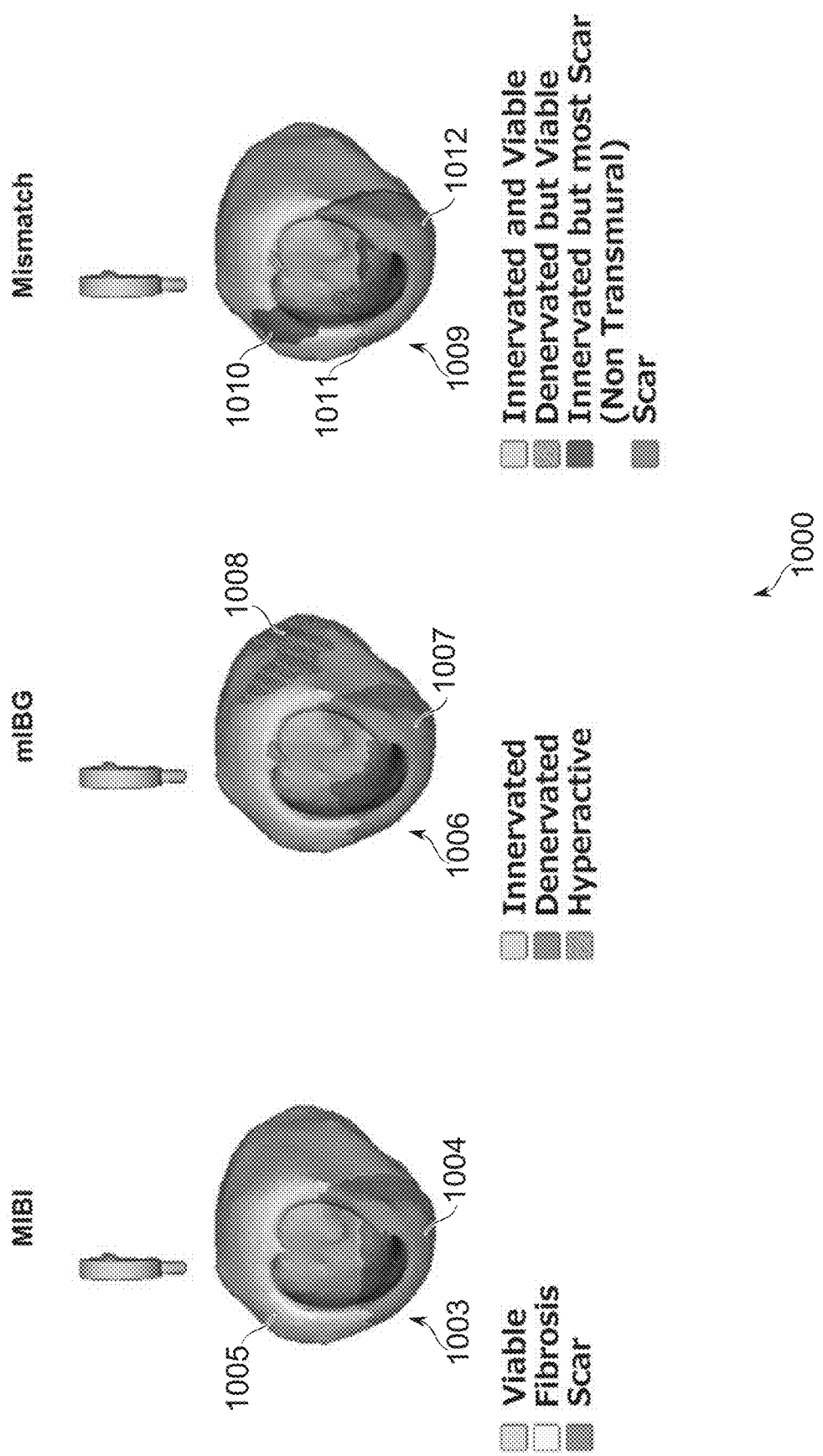
FIG. 10 is a set of nuclear medicine images showing left ventricle tissue zones with scarring and/or abnormal nervous control, according to some exemplary embodiments of the invention.
Figure 11:
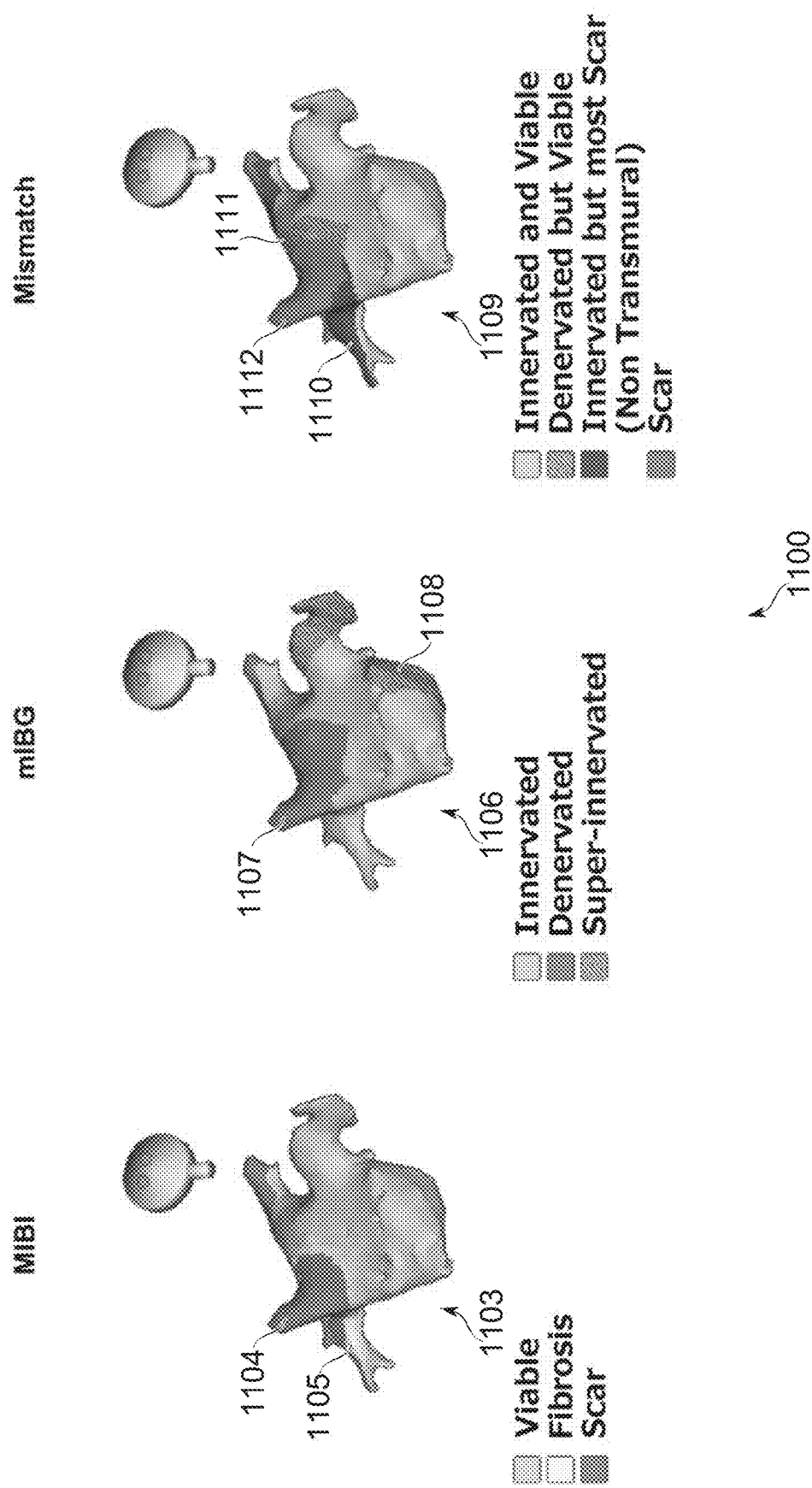
FIGS. 11, 12 and 13 are sets of nuclear medicine images showing left atrium tissue zones with scarring and/or abnormal nervous control, according to some exemplary embodiments of the invention.
Figure 12:
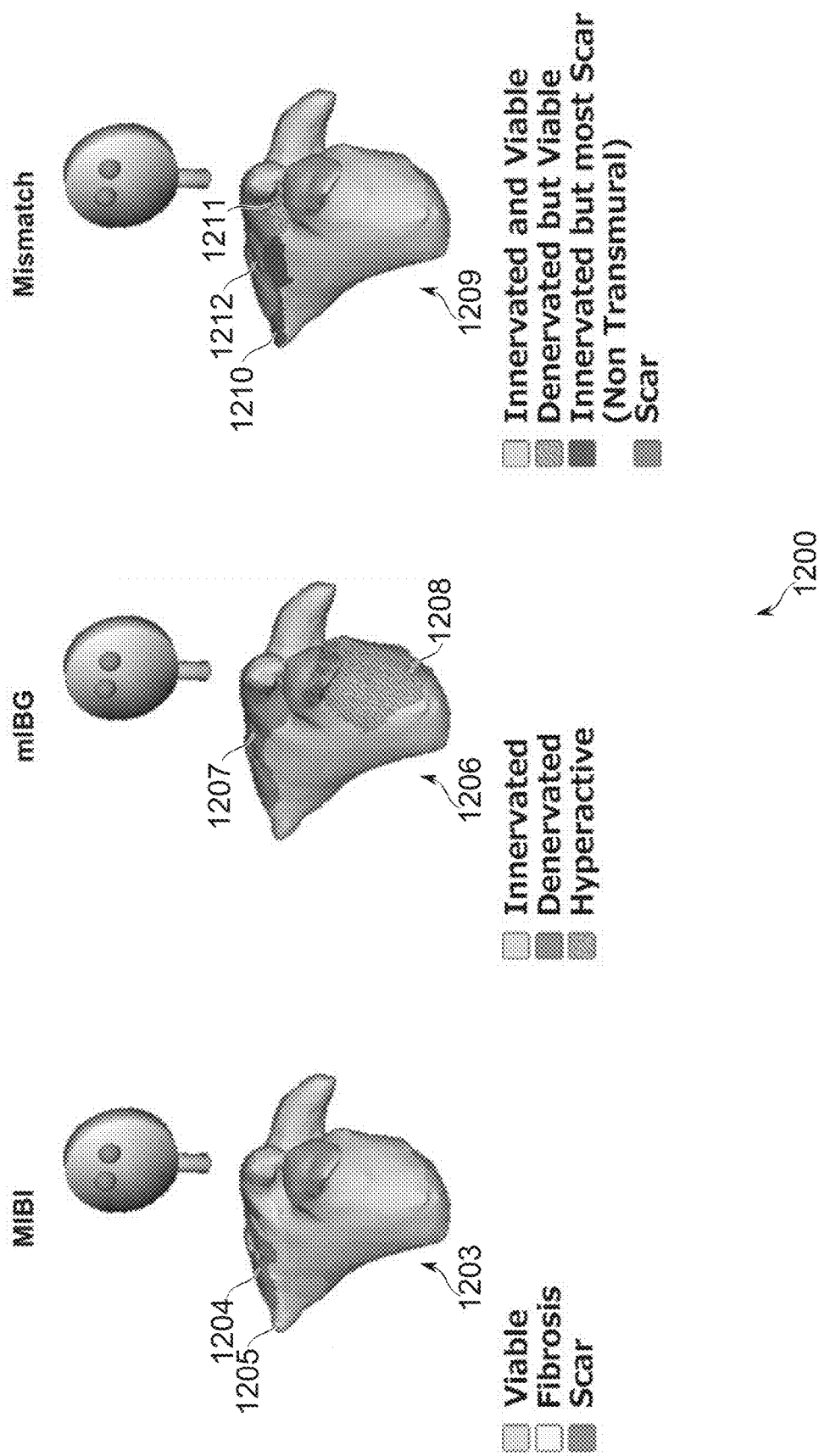
Figure 13:
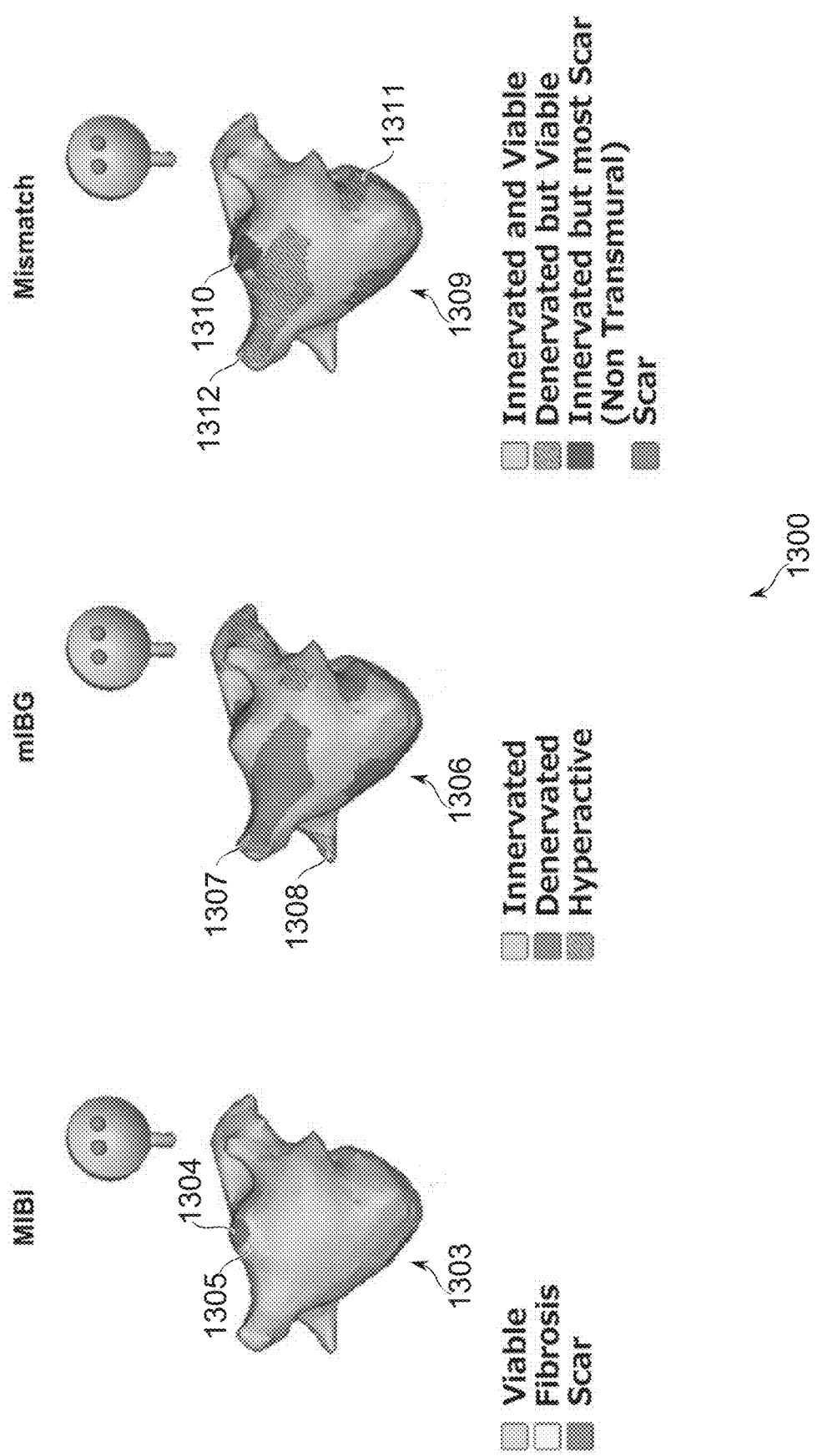

Reference is now made to FIGS. 9 and 11-13, which are sets 900, 1100, 1200, 1300 of nuclear medicine images showing left atrium tissue zones with scarring and/or abnormal nervous control, according to some exemplary embodiments of the invention. Reference is also made to FIG. 10, which is a set 1000, of nuclear medicine images showing left ventricle tissue zones with scarring and/or abnormal nervous control, according to some exemplary embodiments of the invention.

The left images 903, 1003, 1103, 1203 and 1303 each show a radioimage reconstructed using a MIBI tracer (e.g., Sestamibi) which indicates viability. Red (darker) areas 904, 1004, 1104, 1204 and 1304 indicate complete scarring/fibrosis and yellow areas 905, 1005, 1105, 1205 and 1305 indicate partial fibrosis.

The middle images 906, 1006, 1106, 1206 and 1306 each show a radioimage reconstructed using a tracer taken up by nerve endings (e.g., mIBG). Red (darker) areas 907, 1007, 1107, 1207 and 1307 indicate areas with significantly reduced innervation. Yellow/black (hatched) areas 908, 1008, 1108, 1208 and 1308 indicate areas of hyperactive innervation. Hyperactive innervation potentially occurs, for example, if neural tissue acquires a loss of feedback control on growth, maintenance, and/or activity. For example, loss of trophic support due to death of one tissue region potentially encourages excess regrowth in another. Additionally or alternatively, loss of signaling of the effectiveness of innervating activity potentially results from actual tissue death, and/or acquisition of insensitivity by a portion of denervated tissue. In such a case, excess signaling potentially represents a nervous system attempting to counteract the wrong problem.

The right images 909, 1009, 1109, 1209 and 1309 each show what is already visually apparent, which is the very large mismatch between scarring and denervation. In FIGS. 9-13, normalization and display of results is such that four different categories of region are shown: both types of mismatch (greater innervation or greater tissue viability), and matched-healthy, and matched-unhealthy. Specifically, blue (darkest solid) areas 910, 1010, 1110, 1210 and 1310 indicate innervated but less viable tissue; yellow/black (hatched) areas 911, 1011, 1111, 1211 and 1311 indicate denervated but viable tissue; and red (solid, intermediate darkness) areas 912, 1012, 1112, 1212 and 1312 indicate non-innervated, non-viable tissue.

In some cases, innervated but less viable tissue areas 910, 1010, 1110, 1210 and 1310 comprise scarring which is non-transmural; that is, scarring which does not extend entirely across the thickness of the tissue. Before loss of innervation, ANS activity is potentially found on both sides of the heart wall. Optionally, loss of innervation signal from just one side of the wall is considered to be associated with partial scarring, while loss of innervation (and thus of activity signal) on both sides is associated with complete (transmural) scarring. The bulk of inner and outer innervation is either de-excitatory or excitatory for the heart (for example, respectively), which provides another potential method of estimating where damage has occurred to the heart based on properties of the ANS innervation which remains intact.

Remediation of an innervation/vitality imbalance such as is shown in examples of FIGS. 9-13 optionally comprises one or more of the strategies for ablation and/or stimulation described hereinabove. As examples:

a tissue region which has escaped neural control is ablated;

function of a tissue region which has escaped neural control is brought under the control of direct or indirect artificial stimulation, and/or undergoes restoration of innervation, for example by application of trophic factors encouraging regrowth, and/or nerve branch transplantation;

function of a tissue region which has escaped neural control is weakened or paralyzed—for example, stunned and/or dosed with function-blocking drug;

stimulation of a tissue region which is innervated but under-stimulated is enhanced;

a tissue region which remains under neural control, but potentially contributes to organ function instabilities thereby, is denervated, and/or brought under control of artificial stimulation;

a tissue region which remains under neural control, but potentially contributes to organ function instabilities thereby, is weakened, ablated, and/or paralyzed.

a tissue region which remains under neural control, but is insufficiently responsive, is directly or indirectly over-stimulated—for example, by electrode stimulation of the region or its innervation, by transplantation of a nerve branch from another organ region, and/or by dosing with a sensitivity-increasing drug.

In some embodiments of the invention, where ablation is to be performed, a map showing the relative distributions of tissue vitality and tissue innervation is used in illustrating the potential effects of the ablation. For example, a planned ablation is added to a model of the heart tissue. In some embodiments, effects on excitability produced by the planned ablation are modeled. Optionally, modeling is of a range of conditions, for example, of modulated velocities of transmission. In some embodiments, where a potential condition leading to a recurrent transmission characteristic of arrhythmia is detected, an alert to this effect is provided. In some embodiments, modification of the proposed ablation is proposed by the system, based, for example, on iterative changes with remodeling of effects on performance under different operating conditions.

Reference is now made to FIGS. 14A-14D, which illustrate a disease mode of a heart 1400, for which activity imaging provides an understanding which guides a well-localized application of treatment, according to some exemplary embodiments of the invention.

Figure 14A:
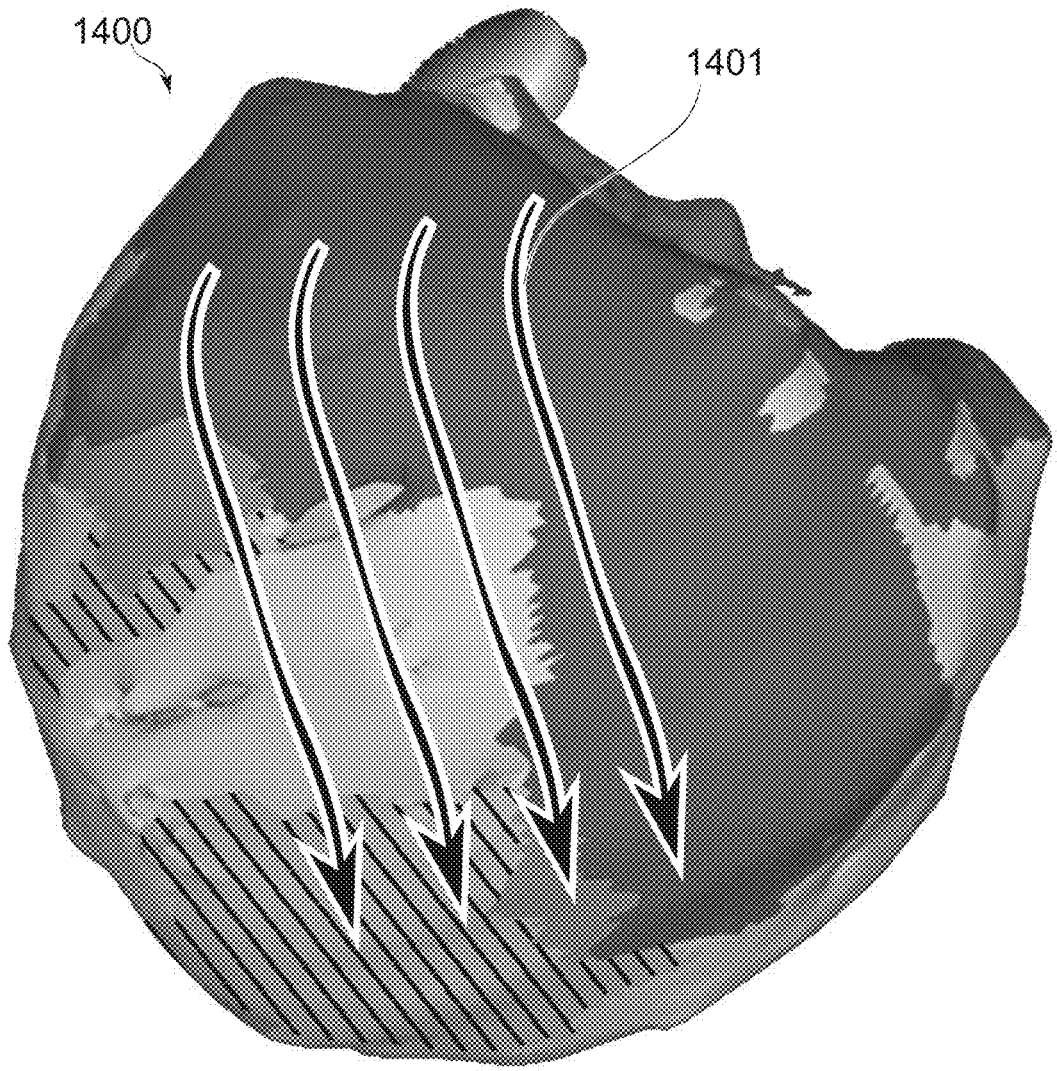
FIGS. 14A, 14B, 14C and 14D illustrate a disease mode of a heart, for which activity imaging provides an understanding which guides a well-localized application of treatment, according to some exemplary embodiments of the invention.
Figure 14B:
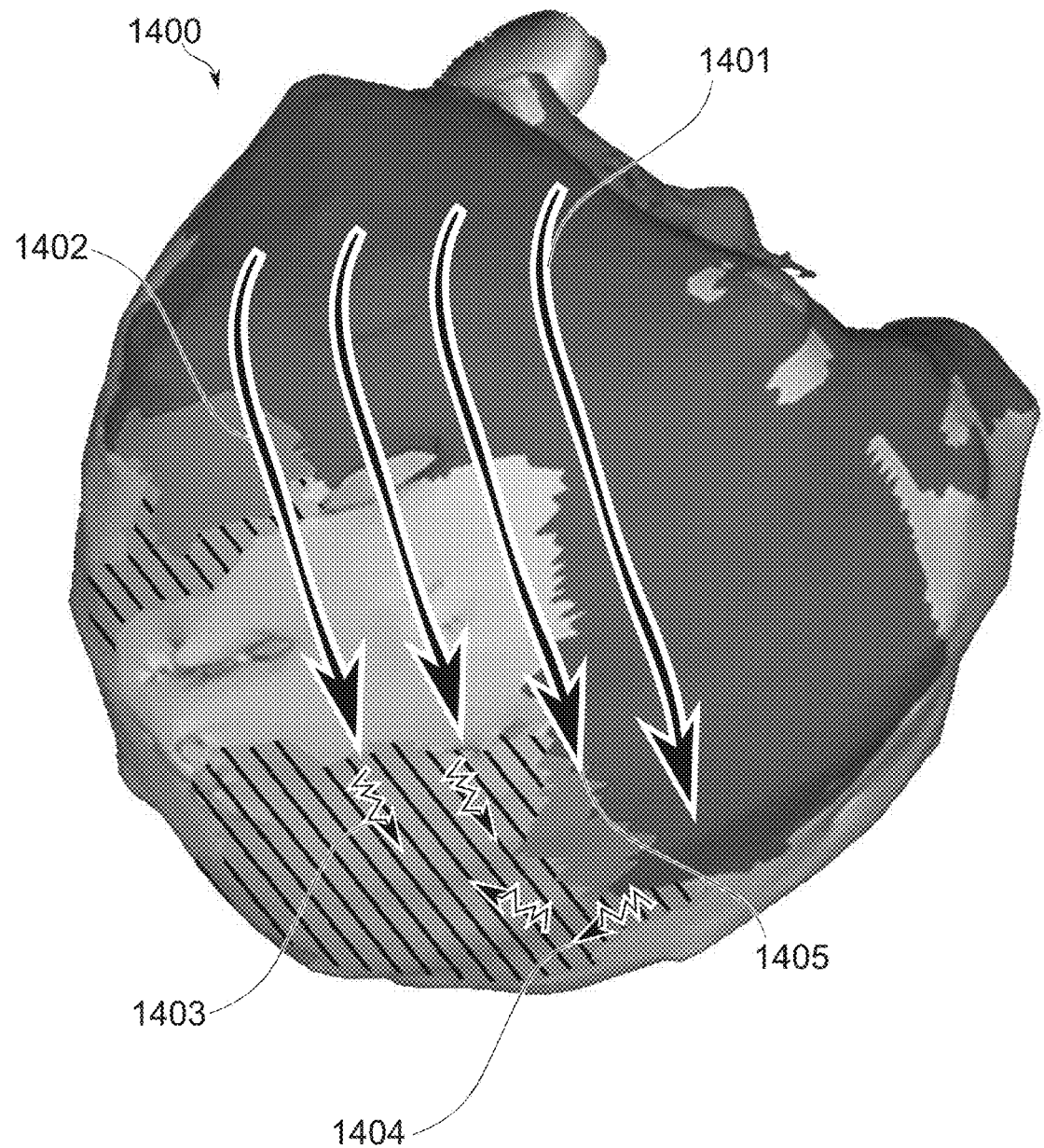

Under a regime of healthy functioning, a heart 1400 contracts according to signaling which propagates across its surface in a relatively orderly wave impulse, as indicated, for example, by arrows 1401 (FIG. 14A). In an exemplary instance of heart damage (FIG. 14B), portion of the impulse 1402, 1405 are disturbed as it passes through a patchwork of denervated (optionally transmural) scarring (red or medium-dark gray), innervated (optionally, non-transmural) scarring (blue or dark gray), healthy (green or light-gray), and denervated but viable (orange-striped or light-gray striped) tissue. Portions of the signaling impulse 1401 remain within healthy tissue, and, accordingly, propagate quickly to distal portions of the heart. Other portions of the impulse soon reach the boundary of a vital but denervated area. When passing into viable, denervated tissue, the impulse 1403 is potentially slowed, for example due to alteration of electrical propagation properties related to the denervation. In normal heart tissue, innervation, together with hormonal influences, acts as a control on conduction velocity (setting the overall pace of heart contractions). However, in denervated tissue, the direct innervating component is lost, typically resulting in a lower basal level of impulse conduction velocity.

At a boundary with non-viable, non-innervated scar tissue, impulse propagation is potentially blocked entirely.

A situation which can potentially arise in such a condition is that a region of tissue is positioned to receive propagation signals from two different directions. For example, in FIG. 14B, a portion of the impulse 1404 proceeds in a retrograde direction from a point which, for example, is just beyond a denervated and scarred region, but adjacent to a region which receives stimulation from an uninterruptedly fast impulse. This mode of operation potentially results in a poorly coordinated contraction, but not necessarily in arrhythmia. However, in some instances, such a condition has a second mode of operation available to it.

Figure 14C:
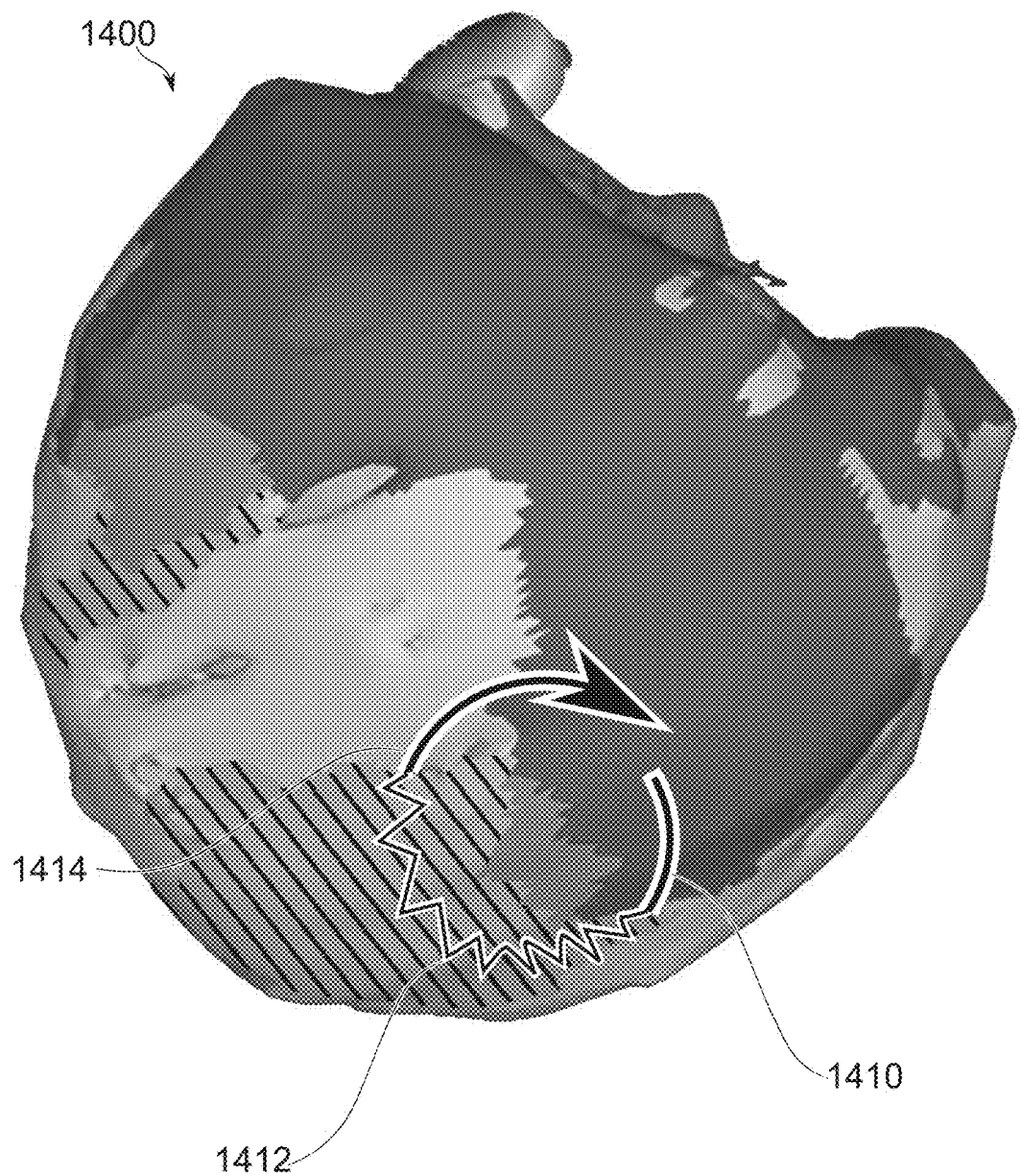

In FIG. 14C, such a mode is shown. Here, as before, a rapidly arriving impulse propagates from region 1410, converting, when crossing to a denervated but viable region, to a slow impulse 1412. However, under some timing conditions, the slow wave continues across the whole of the denervated but viable heart section, to reach a fast-propagating region again, and continue as a fast-propagating impulse 1414.

A difference in timing conditions which can prevent the limiting of the propagation of such an impulse comprises, for example, a sufficient slowing of impulse 1412, such that it reaches the region of impulse 1414 after this region has recovered from its most recent refractory period following contraction. In another example, two normal impulses occur too close together in time (relative to the tissue refractory period), such that the first arrival of the second impulse is blocked by still-refractory tissue. However, the retrograde portion of the second impulse potentially reaches the block region after the refractory period. In either case, or in another configuration, modulation of propagation by ANS tonus potentially is involved in changing the underlying propagation properties of the heart tissue, such that retrograde propagation changes its extent.

In some instances, this pattern of retrograde activation becomes self-reinforcing. For example, the retrograde impulse may reach fast-transmitting tissue again, at a time past its last refractory period. Then the impulse again turns anterograde, and, potentially, the impulse enters a self-stimulating loop. Potentially, this loop resists being broken by normal impulses, by maintaining tissue in a state which is almost always refractory, except for a few moments before the next circular impulse hits it, and/or by creating a back-propagating "wall" of refractory tissue. Thus, the heart potentially enters into a period of cardiac arrhythmia.

In terms of tissue vitality and ANS functional mapping, the hallmarks of one type of potentially arrhythmia-prone configuration have been described: adjacent regions of fast and slow impulse propagation (innervated and denervated), separated by a region inert to impulse propagation. It can be readily understood from this example that other self-reinforcing configurations potentially arise wherever a disturbance to the organization of timing and function has occurred. A particular danger of a fully blocking zone is that it creates a break in the continuity of local propagation, such that adjacent tissue is no longer guaranteed to have a substantially identical refractory period, or even a time of initial activation. In some cases, the fully blocking zone is a normal part of the anatomy (such as a valve ring), the conversion to a fibrillation trigger arising from some other local disruption of vitality and/or innervation.

Figure 14D:
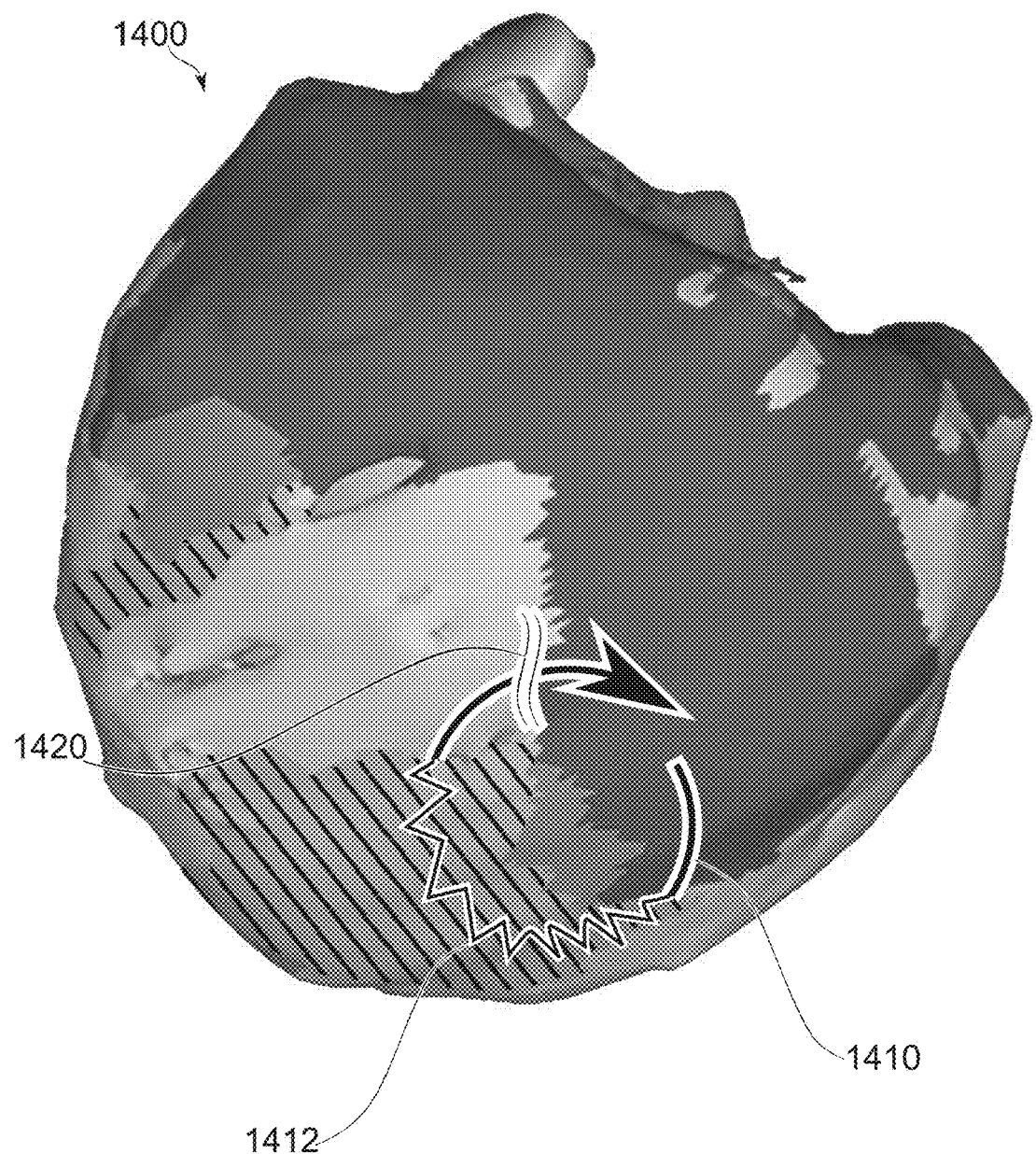

FIG. 14D, in some embodiments, shows how analysis of the ANS functional mapping potentially serves to suggest a treatment which prevents the heart from entering the loop mode of FIG. 14C. An ablation 1420 is made at a region which bisects the pattern of loop activation. Optionally, ablation 1420 is placed at a location which extends an already existing transmural scar to become so long that self-reinforcing propagation can no longer occur. Optionally, an ablation is made to a potentially arrhythmia-generating region which does not comprise a transmural scar already. The potential of a transmural scar region to serve as the focus of an arrhythmia center is in part dependent on its interaction with the timing of impulses that move past it. In some embodiments, a sufficiently long ablation comprises a treatment to prevent a region from generating an arrhythmia, whether or not the region initially comprises a transmural scar. Potentially, the length is determined by the length necessary to prevent retrograde propagation from setting up a resonant cycle.

Figure 15:
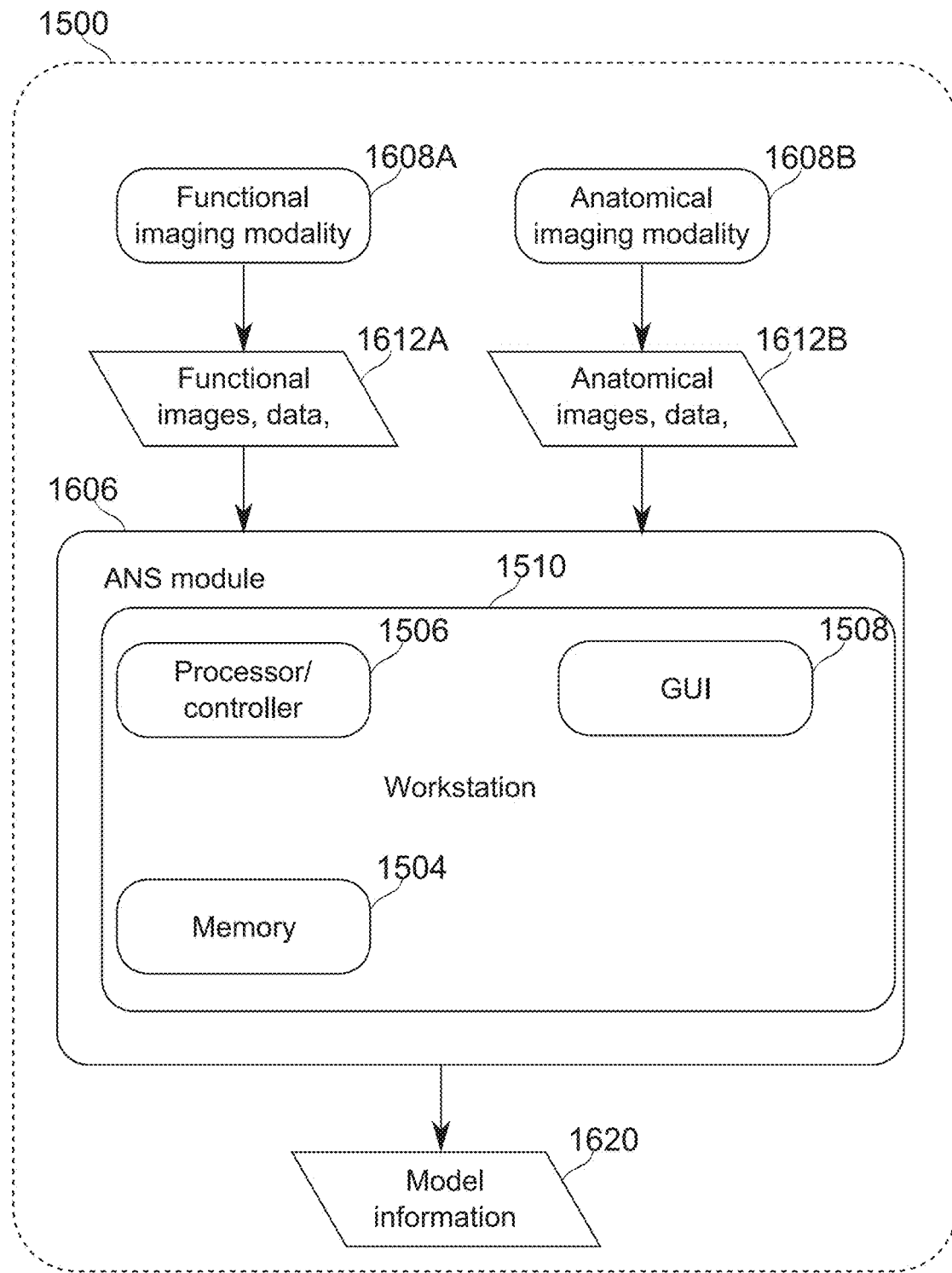
FIG. 15 is a block diagram of a model ANS modeling system/unit, in accordance with some exemplary embodiments of the invention.

Reference is now made to FIG. 15, which is a block diagram of a model ANS modeling system/unit 1606, in accordance with some exemplary embodiments of the invention.

In some embodiments, ANS modeling system/unit 1606 is provided as a part of a system 1500 including functionalities with which ANS modeling system/unit coordinates in series or in parallel. For example, a system 1500 includes a functional imaging modality 1608A (such as a SPECT imager), and/or an anatomical modeling modality 1608B. Anatomical image modality data comprises data obtained, for example, from a CT (X-ray or gamma-ray, for instance), MRI, 3-D ultrasound, 2-D ultrasound, fluoroscopy, or by another modality. Optionally, an ANS modeling system/unit is comprised within another system configuration, such as a system 1600, as described in relation to FIG. 16 hereinbelow.

In some embodiments of the invention, ANS module 1606 receives functional images and/or imaging data 1612A (for example, as produced by functional imaging modality 1608A); and anatomical images and/or imaging data 1612B (for example, as produced by anatomical imaging modality 1608B).

The ANS module itself produces model information 1620 comprising information, about, for example, GP locations, interconnections and/or activity levels. In some embodiments, image data within GP locations resolves one or more distinct and/or identifiable GP regions. Production of an ANS model comprises, for example, one or more of the blocks described in relation to FIG. 3B, hereinabove.

In some embodiments of the invention, ANS module 1606 comprises processor controller 1506. Processor/controller carries out computational tasks of ANS model generation, for example, computational tasks described in relation to FIG. 3B, hereinabove. Optionally, ANS module 1606 is provided with a GUI 1508. In some embodiments, ANS module 1606 comprises memory 1504, used, for example to receive and store images, associated data, model information, and/or process/controller instructions. Optionally, GUI 1508 is used, for example, in the selection of image sources, images, and/or regions of data for analysis. Optionally or alternatively, GUI 1508 is used, for example, to show model results; for example: regions of tissue health or disease, regions of innervation or lack of innervation, regions of nervous system activity/inactivity, and/or any of these regions in relation to one another. In some embodiments, ANS module 1606 comprises a workstation 1510. The workstation itself, in some embodiments, optionally comprises the processor/controller 1506 and/or GUI 1508. In some embodiments, functions of workstation 1510 are distributed; for example, at least a part of ANS modeling carried out by processor/controller 1506 is calculated remotely, for example, as a provided service.

In some embodiments, a system 1500 includes one or more tools for a treatment option such as GP ablation, stimulation, anesthesia, or another neuromodulatory intervention. In some embodiments, system 1500 is operable for guidance of a probe for treatment based on real-time display of a probe and ANS map in registration, direct (for example, robotic) guidance of probe position, or another method of ANSmap-guided treatment and/or treatment probe placement.

Exemplary Diagnosis and Treatment Sub-System

Figure 16:
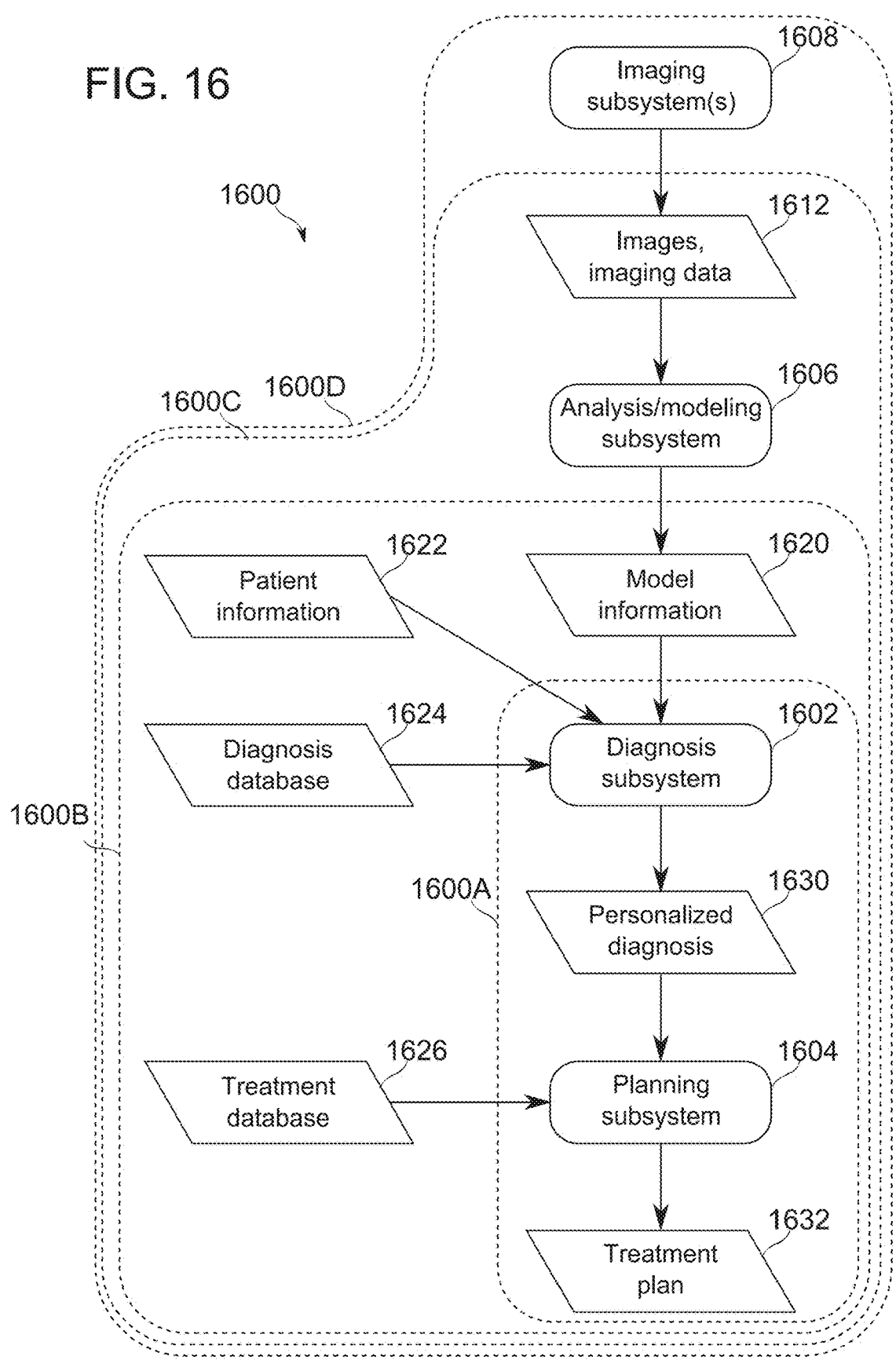
FIG. 16 is a block diagram of a model analysis and treatment planning system/unit, in accordance with some exemplary embodiments of the invention.

Reference is now made to FIG. 16, which is a block diagram of a model analysis and treatment planning system/unit 1600, in accordance with some exemplary embodiments of the invention.

In some embodiments, once a model is available, it is used for diagnosis and/or planning a treatment for example as described hereinabove. Groups of elements comprising a system/unit 1600 include, for example, blocks within the boundaries delineating system configurations 1600A, 1600B, 1600C, 1600D, and/or another system configuration comprising blocks of FIG. 16.

In some embodiments, unit 1600 carries out functions of various model analyses described herein, for example, in relation to FIG. 15. For example, it includes analysis/modeling subsystem 1606, as in configuration 1600C. In some embodiments, unit 1600 is integral to and/or co-located with imaging and/or treatment systems (for example, it includes imaging subsystem(s) 1608, as in configuration 1600D). In some embodiments (for example, including analysis/modeling subsystem 1606), images and imaging data 1612 are received by the system/unit 1600. In some embodiments (for example, including imaging subsystem(s) 1608), images and imaging data 1612 are generated by the system/unit 1600. In some embodiments, imaging subsystems 1608 include an imaging modality described in relation to FIG. 15, for example, a functioning imaging modality 1608A, and/or an anatomical imaging modality 1608B.

In some embodiments, unit 1600 (for example, configurations 1600A and/or 1600B) is remotely located relative to other subsystems, and/or is distributed. Optionally, the functions of, for example, subsystem 1600A are provided as a service. In exemplary embodiments of the invention, rather than provide a user with a model of the ANS 1620, what is provided is a combination model and treatment plan (for example, a combination comprising the information of model information 1620 and treatment plan 1632) or possibly just a treatment plan 1632. Some exemplary treatment plans 1632 are described below.

In a first stage of operation of some embodiments of the invention, model information 1620 and patient information 1622 provided to a diagnosis sub-system 1602. Model information 1620 includes, for example, GP locations, interconnection and/or activity level. Patient information 1622 includes, for example, patient demographics, history and/or previous response to therapy. Optionally, diagnosis sub-system 1602 uses a diagnosis database 1624 to assist in providing a diagnosis. Diagnosis database 1624 includes, for example, rules, example diagnoses, and/or machine learning data. Optionally or alternatively, diagnosis sub-system 1602 includes one or more modules which apply processing on the model to extract diagnose. In some exemplary embodiments of the invention, the diagnosis database 1624 is updatable and/or parts thereof are available at different and/or additional cost.

The output of diagnosis system 1602, in some embodiments, is a personalized diagnosis 1630. In some exemplary embodiments of the invention, the diagnosis database 1624 includes a plurality of templates, each one optionally associated with one or more possible diagnoses and/or including instruction for missing data to assist in diagnosis. Optionally or alternatively, at least one dynamic template is used. Such a template is potentially useful, for example, if a disease is characterized by a temporal pattern of behavior. Such a template includes, for example, multiple snapshots with a time indicator, and/or defines a function of change over time and/or in response to a trigger.

In some exemplary embodiments of the invention, personalized diagnosis 1630 is provided to a planning sub-system 1604. In some embodiments, planning sub-system 1604 generates a treatment plan suitable for the patient, based on the diagnosis and/or best practices. Optionally, a treatment database 1626 is used to aid in treatment planning. The treatment database 1626 includes, for example, exemplary treatments, and/or rules for applying them.

Optionally or alternatively, planning sub-system 1604 uses modules to plan various parts of the treatment and/or to determine if parts of the treatment are reasonable and/or safe. Optionally, model information 1620 and/or patient information 1622 also serve as input for the treatment planning. For example, the information 1620, 1622 is used to help determine what effect a treatment may have on a patient. In some embodiments, the result is a treatment plan 1632.

In some exemplary embodiments of the invention, treatment plan 1632 includes one or more of: a plurality of locations to be treated, an expected measurement for the effect of treatment of a location, treatment parameters for one or more of the location treatments and/or alternatives for one or more of the locations. Optionally, the plan 1632 includes a time line indicating the order of treatment and/or delay times between treatment locations.

In some exemplary embodiments of the invention, a treatment is defined with a time scale of several minutes, hours or days; for example, defining a wait of between 1 and 1010 minutes or between 1 and 20 hours between treatment locations. Waiting allows, for example, the planning of a gradual series of ablations, with observation during the intervals between ablations used to evaluate progress, side-effects, and/or to make planning adjustments according to results achieved.

It should be noted that diagnosis and/or modeling is potentially improved, in some embodiments, by taking into account the effect of treatment. In some exemplary embodiments of the invention, a treatment plan 1632 includes a suggestion to recalculate model and/or diagnosis and/or treatment plan, for example, in response to a measurement exceeding a certain threshold or matching a certain pattern, and/or otherwise to fulfill a rule.

It is expected that during the life of a patent maturing from this application many relevant radioimaging techniques will be developed and the scope of the term radioimaging is intended to include all such new technologies a priori.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A computer implemented method for generating an image map of an organ identifying portions of the organ which are viable and have reduced nervous control, comprising:
   receiving a first image of the organ, wherein the first image indicates viability of the organ;
   receiving a second image of the organ, wherein the second image indicates nervous control of the organ;
   identifying, using a data processor, portions of the organ, each being indicated in the first image to be viable, and indicated in the second image to have a level of nervous control below a predetermined threshold or below normal control levels; and
   generating, using the data processor, an image map of the organ indicating said identified portions.

2. The method according to claim 1, wherein the first image indicates emissions by a first tracer.

3. The method according to claim 2, wherein the second image indicates emissions by a second tracer.

4. The method of claim 3, wherein the organ is a heart.

5. The method of claim 1, wherein the organ is a heart.

6. The method of claim 1, further comprising: identifying a level of viability in a region in the first image based on locations of a tracer selectively taken up by viable tissue of the organ.

7. The method of claim 1, further comprising identifying a level of nervous control of the organ based on locations in the second image of a tracer selectively taken up by at least one of the group consisting of nerve endings and tissue which collects adrenaline.

8. The method of claim 1, wherein the first image and the second image are 4-D images.

9. The method of claim 1, wherein:
   the autonomic nervous control of the portions of the organ with vital non-neural tissue and reduced autonomic nervous control is reduced relative to a normal level of autonomic nervous control; and
   wherein the normal level of autonomic nervous control is provided by an indication of one or more parameter ranges of normal autonomic nervous control comprising at least one of the group consisting of:
a map of normal autonomic nervous control activity ranges allowed for imaged portions of the organ, and
one or more thresholds of autonomic nervous control activity for different parts of the organ.

10. The method of claim 1, wherein the first image and the second image are obtained using dual isotope radioimaging, with a first of the dual isotopes used to identify metabolic activity in the organ, and a second of the dual isotopes used to identify autonomic innervation of the organ based on at least one of the group consisting of activity of presynaptic neurons, the density of receptors for neurotransmitters, and the number of nerve endings.

11. The method of claim 1, wherein the organ comprises the heart of the patient.

12. The method of claim 1, wherein the organ comprises one of the group consisting of: a liver, a kidney, and an organ of the gastrointestinal tract.

13. The method of claim 1, wherein the indicated nervous control of the organ comprises indication of innervation of the organ.

14. The method of claim 13, wherein the indication of innervation comprises an indication of innervation by one or more autonomic ganglia.

15. The method of claim 1, comprising displaying the map.

16. The method of claim 1, comprising presenting treatment guidance, based on the identified portions indicated in the map.

17. The method of claim 16, wherein the treatment guidance indicates a boundary between at least one of the identified portions indicated in the map and another portion of the organ.

18. The method of claim 16, wherein the treatment guidance indicates a mismatch in activity between at least one of the identified portions indicated in the map and another portion of the organ.

* * * * *